United States Patent
Emoto

(10) Patent No.: US 10,501,566 B2
(45) Date of Patent: Dec. 10, 2019

(54) PRODUCTION METHOD OF ALPHA-OLEFIN LOW POLYMER AND PRODUCTION APPARATUS

(71) Applicant: Mitsubishi Chemical Corporation, Chiyoda-ku (JP)

(72) Inventor: Hiroki Emoto

(73) Assignee: Mitsubishi Chemical Corporation, Chiyoda-ku (JP)

(*) Notice: Subject to any disclaimer, the term of this patent is extended or adjusted under 35 U.S.C. 154(b) by 0 days.

(21) Appl. No.: 15/715,545

(22) Filed: Sep. 26, 2017

(65) Prior Publication Data

US 2018/0030181 A1 Feb. 1, 2018

Related U.S. Application Data

(63) Continuation of application No. PCT/JP2016/078610, filed on Sep. 28, 2016.

(30) Foreign Application Priority Data

Sep. 28, 2015 (JP) ................................. 2015-189298

(51) Int. Cl.
*C08F 210/16* (2006.01)
*B01D 5/00* (2006.01)
(Continued)

(52) U.S. Cl.
CPC .............. *C08F 210/16* (2013.01); *B01D 3/14* (2013.01); *C07C 2/08* (2013.01); *C07C 11/107* (2013.01);
(Continued)

(58) Field of Classification Search
None
See application file for complete search history.

(56) References Cited

U.S. PATENT DOCUMENTS 4,408,024 A 10/1983 Matsuyama et al.
5,180,103 A * 1/1993 Harrison, Jr. ........... B05B 1/265
239/1

(Continued)

FOREIGN PATENT DOCUMENTS

EP 0 034 061 A2 8/1981
JP 56-110701 9/1981
(Continued)

OTHER PUBLICATIONS

Heat Exchanger Design Handbook (http://hedhme.com/content_map/?link_id=17449&article_id=262), retrieved on Jun. 25, 2018. Year: 2016).*

(Continued)

*Primary Examiner* — In Suk C Bullock
*Assistant Examiner* — Ali Z Fadhel
(74) *Attorney, Agent, or Firm* — Oblon, McClelland, Maier & Neustadt, L.L.P.

(57) ABSTRACT

The present invention relates to a method and an apparatus for producing an α-olefin low polymer by subjecting an α-olefin to low polymerization reaction in the presence of a catalyst in a liquid phase part within a reactor, and the present invention relates to a method and an apparatus for producing an α-olefin low polymer, such as 1-hexene, etc., by subjecting an α-olefin, such as ethylene, etc., to low polymerization reaction, in which the formation of a polymer on an upper tube plate surface of a shell and tube type heat exchanger that is used for heat removal is suppressed, thereby performing a continuous operation stably over a long period of time.

22 Claims, 11 Drawing Sheets

(51) Int. Cl.

| | | |
|---|---|---|
| *C07C 11/107* | (2006.01) | |
| *F28G 9/00* | (2006.01) | |
| *F28D 7/16* | (2006.01) | |
| *B01D 3/14* | (2006.01) | |
| *C07C 2/08* | (2006.01) | |
| *C08F 10/02* | (2006.01) | |
| *C07C 2/32* | (2006.01) | |
| *F28F 9/02* | (2006.01) | |
| *F28G 1/16* | (2006.01) | |
| *F28D 21/00* | (2006.01) | |

(52) U.S. Cl.
  CPC .......... *C08F 10/02* (2013.01); *C08F 2500/02* (2013.01); *C08F 2500/03* (2013.01); *C08F 2500/07* (2013.01)

(56) References Cited

U.S. PATENT DOCUMENTS

| | | |
|---|---|---|
| 5,625,012 A | 4/1997 | Hussein et al. |
| 5,733,988 A | 3/1998 | Apecetche et al. |
| 5,750,816 A | 5/1998 | Araki et al. |
| 2002/0176812 A1 | 11/2002 | Takai et al. |
| 2004/0122271 A1 | 6/2004 | Van Zon et al. |

FOREIGN PATENT DOCUMENTS

| | | |
|---|---|---|
| JP | 62-263205 | 11/1987 |
| JP | 8-239419 | 9/1996 |
| JP | 11-322810 | 11/1999 |
| JP | 2002-338607 | 11/2002 |
| JP | 2004-244527 | 9/2004 |
| JP | 2006-500412 | 1/2006 |
| JP | 2009-120588 | 6/2009 |
| JP | 2014-177423 | 9/2014 |
| JP | 2014177423 A * | 9/2014 |
| JP | 2015-189740 | 11/2015 |
| WO | WO 98/20046 A1 | 5/1998 |

OTHER PUBLICATIONS

International Search Report dated Nov. 29, 2016 in PCT/JP2016/078610, filed on Sep. 28, 2016 (with English Translation).

Written Opinion dated Nov. 29, 2016 in PCT/JP2016/078610, filed on Sep. 28, 2016.

* cited by examiner

(DROPLETS ATTACH SUBSTANTIALLY UNIFORMLY OVER THE ENTIRETY)

✕
(DROPLETS ATTACH HETEROGENEOUSLY)

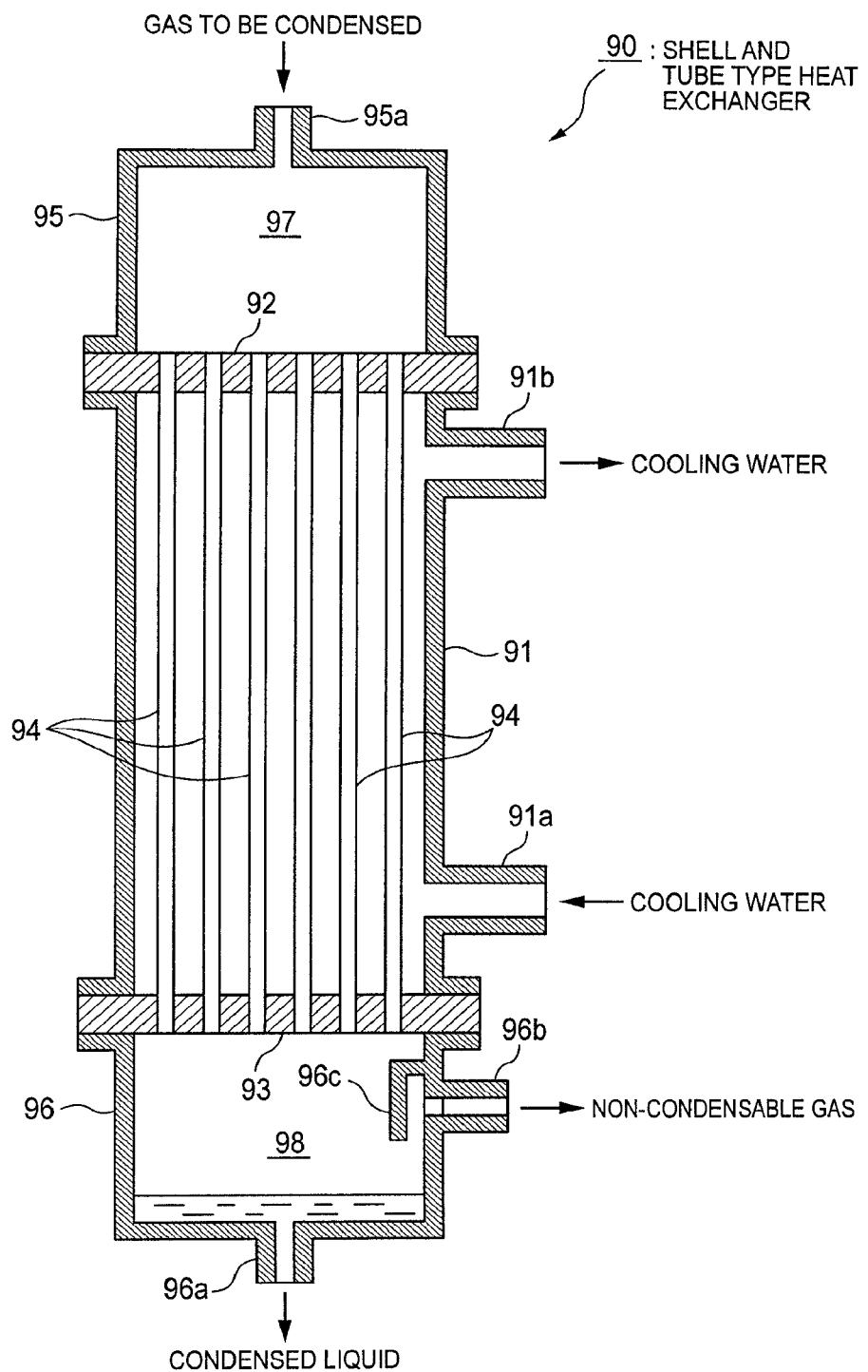

PRODUCTION METHOD OF ALPHA-OLEFIN LOW POLYMER AND PRODUCTION APPARATUS

CROSS-REFERENCE TO RELATED APPLICATIONS

This application is a Continuation of PCT/JP2016/078610, which was filed on Sep. 28, 2016. This application is based upon and claims the benefit of priority to Japanese Application No. 2015-189298, which was filed on Sep. 28, 2015.

TECHNICAL FIELD

The present invention relates to a method and an apparatus for producing an α-olefin low polymer by subjecting an α-olefin to low polymerization reaction in the presence of a catalyst in a liquid phase part within a reactor. In more detail, the present invention relates to a method and an apparatus for producing an α-olefin low polymer, such as 1-hexene, etc., by subjecting an α-olefin, such as ethylene, etc., to low polymerization reaction, in which the formation of a polymer on an upper tube plate surface of a shell and tube type heat exchanger (also referred to as a multi-tube type heat exchanger) that is used for heat removal is suppressed, thereby performing a continuous operation stably over a long period of time.

BACKGROUND ART

An α-olefin low polymer is a useful substance that is widely used as a monomer raw material of olefin-based polymers, as a comonomer of various polymers, and as a raw material of plasticizers, surfactants, lubricating oils, and so on. In particular, 1-hexene obtained by low polymerization reaction of ethylene is useful as a raw material linear low-density polyethylene.

The α-olefin low polymer is typically produced by a method of subjecting an α-olefin to low polymerization reaction in the presence of a catalyst and a solvent.

For example, Patent Document 1 describes a method of producing an α-olefin low polymer composed mainly of 1-hexene in a high yield and a high selectivity by using a chromium-based catalyst and an n-heptane solvent.

Since the low polymerization reaction for obtaining an α-olefin low polymer composed mainly of 1-hexene is an exothermic reaction, there have hitherto been studied industrial methods for continuously producing an α-olefin low polymer while removing reaction heat generated within a reactor.

Patent Document 2 describes a method of producing an α-olefin oligomer having an average molecular weight of 50 to 350 by oligomerization of the ethylene in the presence of a catalyst, in which a gas of a gas phase within a reactor is used as a coolant, a part of the gas of the gas phase within the reactor is cooled by a condenser not coming into direct contact with a liquid phase, and the polymerization heat is removed by a condensed liquid.

In addition, Patent Document 3 describes a method of producing an α-olefin low polymer, in which a gas within a reactor is introduced into a heat exchanger, a condensed liquid obtained from an outlet of the heat exchanger and the gas are circulated into the reactor and describes that in order to suppress the entrainment of a reaction liquid in a gas phase part, a linear gas velocity of the gas phase part within the reactor is controlled to a predetermined range.

The shell and tube type heat exchanger that is used in the present invention has a structure in which a large number of pipes (tubes) are disposed in a hermetically sealed outer cylinder (shell) and is also called a tubular condenser, and in view of the fact that a wide heat transfer area can be ensured in a small capacity, it is also industrially used as a cooling condenser of gas. For example, Patent Document 4 describes a shell and tube type heat exchanger applied for a recovering apparatus of a polymerizable monomer vapor.

FIG. 11 is a schematic vertical cross-sectional view of a conventional vertical shell and tube type heat exchanger 90.

This heat exchanger 90 includes a cylindrical shell (trunk part) 91 whose cylinder axial direction is set in the vertical direction; an upper tube plate 92 and a lower tube plate 93 disposed on the upper side and the lower side of the shell 91, respectively; a large number of tubes 94 installed between the tube plates 92 and 93; a top cover 95 disposed on the upper side of the upper tube plate 92; and a bottom cover 96 disposed on the lower side of the lower tube plate 93. A gas supply nozzle 95a of a gas to be condensed is provided in the top of the top cover 95, and a takeout port 96a of a condensed liquid is provided in the bottom of the bottom cover 96.

In addition, a discharge port 96b of a non-condensable gas is provided on the side face of the bottom cover 96, and a cover 96c for preventing outflow of a condensed liquid is provided inside of the bottom cover 96 of an opening of this discharge port 96b.

In addition, an inflow port 91a of cooling water is provided in a lower portion of the side face of the shell 91, and an outflow port 91b of cooling water is provided in an upper side thereof.

The peripheries of the tube plates 92 and 93 are sandwiched between flanges (symbols omitted) provided on the lower end of the top cover 95, the both upper and lower ends of the shell 91, and the upper end of the bottom cover 96 and fixed by bolts (illustration omitted) penetrating therethrough.

The interior of each of the tubes 94 not only communicates with the interior of a reception chamber 97 surrounded by the upper tube plate 92 and the top cover 95 but also communicates with the interior of a takeout chamber 98 surrounded by the lower tube plate 93 and the bottom cover 96. The upper end and lower end of each of the tubes 94 are fixed to the tube plates 92 and 93, respectively by means of welding or the like.

The gas to be condensed flows into in the reception chamber 97 from the gas supply nozzle 95a and passes through the interior of each of the tubes 94. During a time when the gas to be condensed passes through the interior of the tube 94, it is cooled by cooling water and condensed, and the condensed liquid goes through the takeout chamber 98 and is then withdrawn from the takeout port 96a. The non-condensable gas is discharged from the discharge port 96b.

There is also a case where the reception chamber 97 of the gas to be condensed is provided with an impact plate (baffle plate) in order to disperse the gas to be condensed having flown thereinto against the side of the upper tube plate 92.

BACKGROUND ART DOCUMENT

Patent Document

Patent Document 1: JP-A-H08-239419
Patent Document 2: JP-T-2006-500412
Patent Document 3: JP-A-2009-120588
Patent Document 4: JP-A-2004-244527

SUMMARY OF INVENTION

Problem that Invention is to Solve

As described previously, since the reaction for obtaining an α-olefin low polymer using an α-olefin, such as ethylene, etc., as a raw material is an endothermic reaction, it is needed to remove this reaction heat. Since substances causing a stain, such as a polymer, a catalyst, etc., are present in the reaction liquid, the heat removal method is preferably a method in which a gas in a gas phase part within a reactor, having an extremely minute amount of such substances causing a stain, is withdrawn, and then cooled and condensed by the shell and tube type heat exchanger as shown in FIG. 11, and the condensed liquid and non-condensable gas are circulated into the reactor.

However, even in this case, a mist of the catalyst-containing reaction liquid generated when air bubbles rupture on the gas-liquid interface of the reactor is entrained together with the gas and attaches onto the surface of the upper tube plate 92 of the heat exchanger 90. Thereafter, in view of the matter that the catalyst retains on the surface of the tube plate 92 over a long period of time, a polymer is formed on the surface of the tube plate 92, and the polymer plugs the inlets of the heat exchanger tubes 94. Thus, the circulation of the gas is hindered, and the cooling efficiency is lowered. In an extreme case, it becomes impossible to continue the operation because of plugging of the tubes 94. In particular, as a partial pressure of the α-olefin of the gas to be supplied into the heat exchanger is higher, the amount of formation of the polymer to be caused due to the retained catalyst increases, whereby it becomes difficult to perform the continuous operation stably over a long period of time.

The present invention is to solve the foregoing problem in the production of an α-olefin low polymer.

That is, a problem of the present invention is to provide a method and an apparatus for producing an α-olefin low polymer, in which the formation of a polymer on the surface of an upper tube plate of a shell and tube type heat exchanger that is used for heat removal is suppressed, thereby making it possible to achieve a continuous operation stably over a long period of time.

Means for Solving Problem

In order to solve the foregoing problem, the present inventor made extensive and intensive investigations. As a result, it has been found that by not only controlling a density and a flow rate of a gas to be condensed that is supplied into a shell and tube type heat exchange but also supplying atomized droplets for cleaning onto the surface of an upper tube plate, the surface of the upper tube plate can be effectively cleaned, and as a result, long-term retention of a catalyst-containing mist is prevented from occurring, whereby the formation of a polymer to be caused due to the retained catalyst is suppressed, and it becomes possible to achieve a stable continuous operation over a long period of time, leading to accomplishment of the present invention.

Specifically, the gist of the present invention is as follows.
[1] A method for producing an α-olefin low polymer by subjecting an α-olefin to low polymerization reaction in the presence of a catalyst, the method comprising:

a step of withdrawing a gas of a gas phase part within a reactor, introducing the gas for cooling into a shell and tube type heat exchanger, and circulating and supplying an obtained condensed liquid into the reactor, wherein the heat exchanger includes jet nozzles for supplying atomized droplets between a gas supply port and a tube plate, the gas is supplied as a gas having a density of 20 kg/m$^3$ or more at a gas flow rate of 1 m/s or more from the gas supply port, and the atomized droplets are supplied from the jet nozzles provided in five or more places per 1.00 m$^2$ of an area of the tube plate.

[2] A method for producing an α-olefin low polymer by subjecting an α-olefin to low polymerization reaction in the presence of a catalyst within a reactor, the method comprising:

a step of withdrawing a part of a gas of a gas phase part within a reactor, introducing the gas for cooling into a shell and tube type heat exchanger, and circulating and supplying an obtained condensed liquid into the reactor, wherein the heat exchanger includes: a cylindrical shell; an upper tube plate and a lower tube plate disposed on an upper end side and a lower end side of the shell, respectively; a large number of tubes installed between the upper tube plate and the lower tube plate; a top cover disposed on the upper side of the upper tube plate; a bottom cover disposed on the lower side of the lower tube plate; a gas supply nozzle of a gas to be condensed provided in the top cover; and a takeout port of a condensed liquid provided in the bottom of the bottom cover, and during a time when the gas to be condensed passes through the interior of the tube, the gas to be condensed is cooled to convert into a condensed liquid, the gas withdrawn from the gas phase part of the reactor is introduced as a gas having a density of 20 kg/m$^3$ or more at a gas flow rate of 1 m/s or more from the gas supply nozzle, and the atomized droplets are supplied from the jet nozzles provided in five or more places per 1.00 m$^2$ of an area of the upper tube plate onto the surface of the upper tube plate.

[3] The method for producing an α-olefin low polymer as described in [1] or [2], wherein the atomized droplets contain at least one component that is condensed within the shell and tube type heat exchanger.

[4] The method for producing an α-olefin low polymer as described in any one of [1] to [3], wherein a Sauter mean diameter of the atomized droplets is 3 mm or less.

[5] The method for producing an α-olefin low polymer as described in any one of [1] to [4], wherein the jet nozzles are a spray nozzle.

[6] The method for producing an α-olefin low polymer as described in any one of [1] to [5], wherein the α-olefin is ethylene. [7] The method for producing an α-olefin low polymer as described in any one of [1] to [6], wherein the jet nozzles are installed protruded within the top cover of the heat exchanger, and a direction of a part of the jet nozzles is inclined to a direction directing to the gas supply port or the gas supply nozzle from the horizontal direction.

[8] The method for producing an α-olefin low polymer as described in any one of [1] to [7], wherein the jet nozzles are a full cone spray nozzle.

[9] The method for producing an α-olefin low polymer as described in [8], wherein a spray angle of the full cone spray nozzle is 15° to 170°.

[10] An apparatus for producing an α-olefin low polymer by subjecting an α-olefin to low polymerization reaction, the apparatus comprising:

a reactor in which a catalyst and an α-olefin are supplied to perform low polymerization reaction of the α-olefin;

a shell and tube type heat exchanger in which a gas withdrawn from a gas phase part within the reactor is cooled to obtain a condensed liquid; and a circulating and supplying means in which the condensed liquid obtained in the heat exchanger is circulated and supplied into the reactor, wherein the heat exchanger includes: a cylindrical shell; an upper tube plate and a lower tube plate disposed on an upper end side and a lower end side of the shell, respectively; a large number of tubes installed between the upper tube plate and the lower tube plate; a top cover disposed on the upper side of the upper tube plate; a bottom cover disposed on the lower side of the lower tube plate; a gas supply nozzle of a gas to be condensed provided in the top cover; and a takeout port of a condensed liquid provided in the bottom of the bottom cover, and during a time when the gas to be condensed passes through the interior of the tube, the gas to be condensed is cooled to convert into a condensed liquid, the gas withdrawn from the gas phase part of the reactor is introduced as a gas having a density of 20 kg/m$^3$ or more at a gas flow rate of 1 m/s or more from the gas supply nozzle, and the top cover is provided with jet nozzles for supplying atomized droplets onto the surface of the upper tube plate in five or more places per 1.00 m$^2$ of an area of the upper tube plate.

[11] The apparatus for producing an α-olefin low polymer as described in [10], wherein the atomized droplets contain at least one component that is condensed within the shell and tube type heat exchanger.

[12] The apparatus for producing an α-olefin low polymer as described in [10] or [11], wherein a Sauter mean diameter of the atomized droplets is 3 mm or less.

[13] The apparatus for producing an α-olefin low polymer as described in any one of [10] to [12], wherein the jet nozzles are a spray nozzle.

[14] The apparatus for producing an α-olefin low polymer as described in any one of [10] to [13], wherein the jet nozzles are installed protruded within the top cover, and a direction of a part of the jet nozzles is inclined to a direction directing to the gas supply nozzle from the horizontal direction.

[15] The apparatus for producing an α-olefin low polymer as described in any one of [10] to [14], wherein the jet nozzles are a full cone spray nozzle.

[16] The apparatus for producing an α-olefin low polymer as described in [15], wherein a spray angle of the full cone spray nozzle is 15° to 170°.

Effects of Invention

In accordance with the present invention, in producing an α-olefin low polymer, the formation of a polymer on the surface of the upper tube plate in the shell and tube type heat exchange for heat removal of the reaction heat is suppressed, and it becomes possible to perform a continuous operation stably over a long period of time.

BRIEF DESCRIPTION OF DRAWINGS

FIG. 3A to FIG. 3D are views showing a spray nozzle set used in Example 1, in which FIG. 3A is a perspective view, FIG. 3B is a front view, FIG. 3C is a plan view, and FIG. 3D is a bottom view.

FIG. 6A to FIG. 6C are views showing a spray nozzle set used in Example 8, in which FIG. 6A is a front view, FIG. 6B is a plan view, and FIG. 6C is a bottom view.

FIG. 11 is a schematic vertical cross-sectional view of a vertical shell and tube type heat exchanger.

MODE FOR CARRYING OUT INVENTION

Embodiments of the present invention are hereunder described in detail. The present invention is not limited to the following embodiments and can be carried out with various modifications within a scope of its gist. In addition, the drawings used are to explain the present embodiments and do not show the actual size.

[Production Step of α-Olefin Low Polymer]

Figure 1:
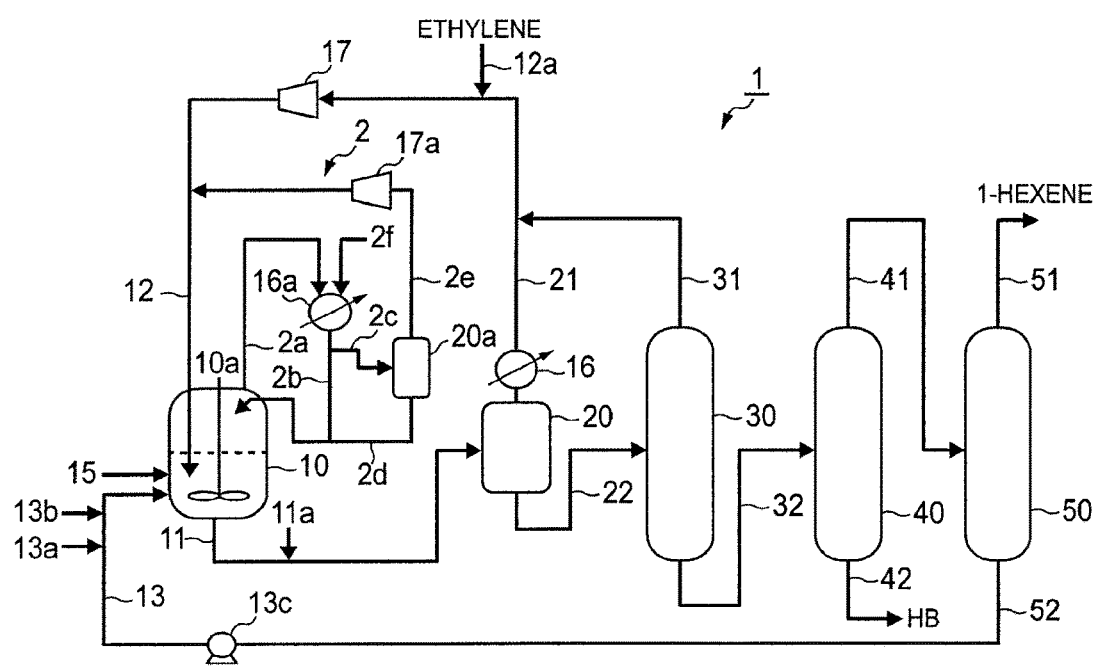
FIG. 1 is a process flow diagram showing an embodiment of a production method and a production apparatus of an α-olefin low polymer according to the present invention.

First of all, a production step of an α-olefin low polymer according to the present invention is explained by reference to FIG. 1 showing an embodiment of a production method and a production apparatus of an α-olefin low polymer according to the present invention. A raw material α-olefin, a catalyst, a reaction solvent, and so on in the present invention are described later.

In the following explanation, the present invention is explained by exemplifying production of 1-hexene (trimer of ethylene) mainly using ethylene as an α-olefin, but the present invention is by no means limited to the production of 1-hexene from ethylene.

A production apparatus 1 of 1-hexene shown in FIG. 1 is provided with, as main apparatuses, a completely mixing type reactor 10 in which ethylene is subjected to low polymerization reaction in the presence of a catalyst, such as a chromium-based catalyst, etc., and a reflux condensation system 2 in which an ethylene gas within the reactor 10 and a vapor component evaporated from a liquid phase are cooled and condensed.

In addition, the production apparatus 1 includes a degassing tank 20 that separates an unreacted ethylene gas from a reaction liquid withdrawn from the reactor 10, an ethylene separation column 30 that distills ethylene in the reaction liquid withdrawn from the degassing tank 20, a high boiling separation column 40 that separates substances with a higher boiling point (hereinafter sometimes referred to as "HB" (high boiler)) in the reaction liquid withdrawn from the ethylene separation column 30, and a hexene separation column 50 that distills the distillate withdrawn from the column top of the high boiling separation column 40 to distill 1-hexene.

In the apparatus shown in FIG. 1, the raw material ethylene is continuously supplied into the reactor 10 from an ethylene supply pipe 12a via a compressor 17 and a first supply pipe 12. Into this compressor 17, unreacted ethylene separated in the degassing tank 20 and a heat exchanger (condenser) 16 is introduced via a circulating piping 21, ethylene separated by the ethylene separation column 30 is also introduced via a circulating piping 31 and circulated into the reactor 10 as the raw material ethylene together with ethylene from the ethylene supply pipe 12a.

On the other hand, a reaction solvent that is used for the low polymerization reaction of ethylene is supplied from a second supply pipe 13 into the reactor 10. This reaction solvent is one separated and recovered in the latter-stage hexene separation column 50. Into this second supply pipe 13, among the catalyst components, a transition metal-containing compound and a nitrogen-containing compound are supplied via a catalyst supply pipe 13a, and a halogen-containing compound is supplied via a catalyst supply pipe 13b, and these compounds are introduced into the reactor 10 together with the reaction solvent.

In addition, an aluminum-containing compound is introduced directly into the reactor 10 from a third supply pipe 15. The aluminum-containing compound may be supplied into the reactor 10 after being diluted with the reaction solvent of the second supply pipe 13 prior to the catalyst components being supplied from the catalyst supply pipes 13a and 13b (not illustrated). It is preferred that these catalyst components are supplied into the liquid phase part within the reactor 10.

On the occasion of circulating and supplying the reaction solvent from the hexene separation column 50 into the reactor 10, at least a part of the reaction solvent of the second supply pipe 13 prior to the catalyst components being supplied from the catalyst supply pipes 13a and 13b may also be dispersed and supplied as a droplet into the gas phase part of the reactor 10. As a supply mode, the same mode as in a condensed liquid from a heat exchanger 16a as described later can be adopted.

As the reactor 10, there is, for example, exemplified a conventionally well-known reactor equipped with a stirring machine 10a, a baffle, a jacket, and the like. As the stirring machine 10a, a stirring blade of the type, such as a paddle, a pfaudler, a propeller, a turbine, etc., is used in combination with a baffle, such as a planar plate, a cylinder, a hairpin coil, etc.

The reflux condensation system 2 includes a heat exchanger 16a in which an ethylene gas introduced into the liquid phase of the reactor 10 and an evaporated vapor from the liquid phase are introduced via a piping 2a, and then cooled and condensed; a gas-liquid separator 20a in which a part of the condensed liquid and a part of the non-condensable gas component obtained in the heat exchanger 16a are introduced via a piping 2c and separated into a condensed liquid and a gas component; and a blower 17a in which the gas component separated in the gas-liquid separator 20a is introduced into the liquid phase of the reactor 10 via a piping 2e and the first supply pipe 12.

The condensed liquid obtained in the heat exchanger 16a and the condensed liquid separated in the gas-liquid separator 20a are introduced into the reactor 10 via pipings 2b and 2d, respectively.

That is, a mixed gas of the ethylene gas introduced into the liquid phase part within the reactor 10 and the evaporated vapor resulting from evaporation of a part of the liquid phase by polymerization heat generated by the low polymerization reaction of ethylene within the reactor 10 (gas of the gas phase part within the reactor, hereinafter also referred to as "supply gas") is supplied into the heat exchanger 16a via the piping 2a. In the case where a temperature of the mixed gas supplied into the heat exchanger 16a is 100° C. or higher, the mixed gas is cooled and condensed with cooling water (not illustrated) to typically lower than 100° C., preferably 80° C. or lower, and more preferably 70° C. or lower, and the condensed liquid is again circulated and supplied into the reactor 10 via the piping 2b. In addition, a part of the gas component obtained from an outlet of the heat exchanger 16a is supplied via the piping 2c and separated into ethylene and a condensed liquid in the gas-liquid separator 20a, and the ethylene is circulated and supplied into the liquid phase part of the reactor 10 by the blower 17a via the piping 2e and the first supply pipe 12. In addition, the condensed liquid is circulated and supplied into the reactor 10 via the piping 2d.

The heat exchanger of the present invention is a shell and tube type heat exchanger and is preferably of a vertical type. This vertical shell and tube heat exchanger includes a cylindrical shell; an upper tube plate and a lower tube plate disposed on the upper end side and the lower end side of the shell, respectively; a large number of tubes installed between the upper tube plate and the lower tube plate; a top cover disposed on the upper side of the upper tube plate; a bottom cover disposed on the lower side of the lower tube plate; a gas supply nozzle of a gas to be condensed provided in the top cover; and a takeout port of a condensed liquid provided in the bottom of the bottom cover. The heat exchanger of the present invention has plural tubes, and the number of tubes can be arbitrarily selected depending on the size and shape of the heat exchanger, the intended use thereof and the like.

The heat exchanger 16a of the reflux condensation system 2 of the present invention is hereunder explained by reference to FIG. 2A and FIG. 2B.

Figure 2A:
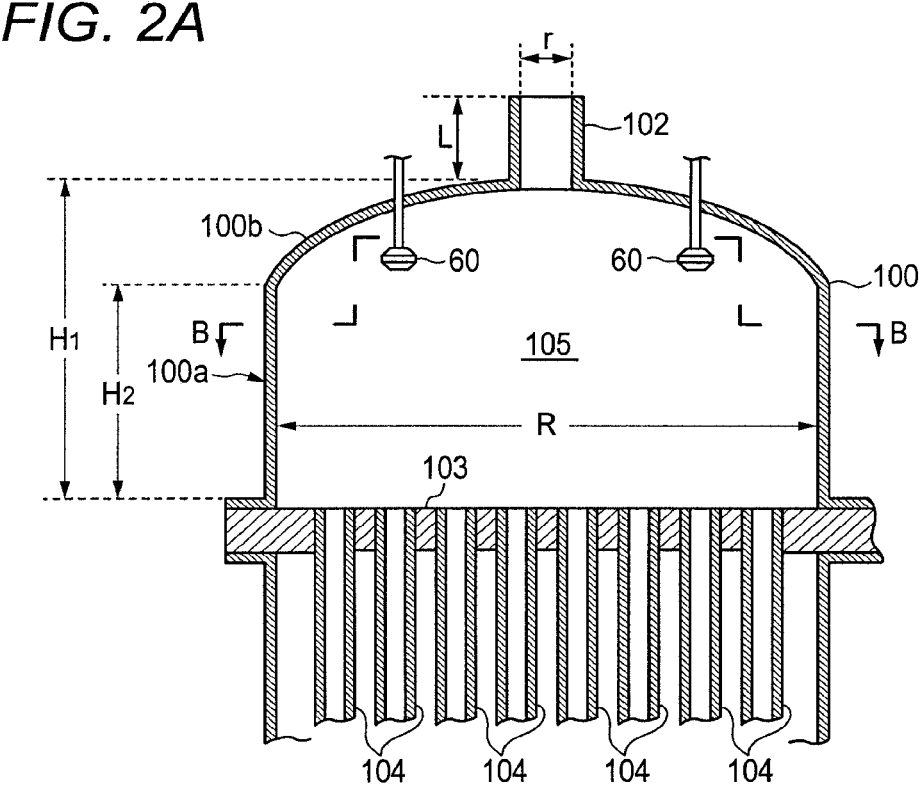
FIG. 2A is a vertical cross-sectional view showing an example of a configuration of a top cover and an upper tube plate portion of a vertical shell and tube type heat exchanger that is used in the present invention.
Figure 2B:
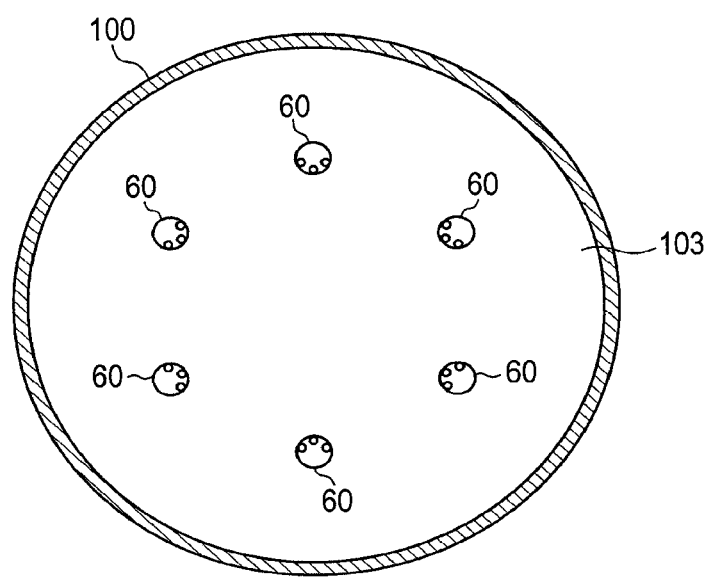
FIG. 2B is a horizontal cross-sectional view along a B-B line of FIG. 2A.
Figure 3A:
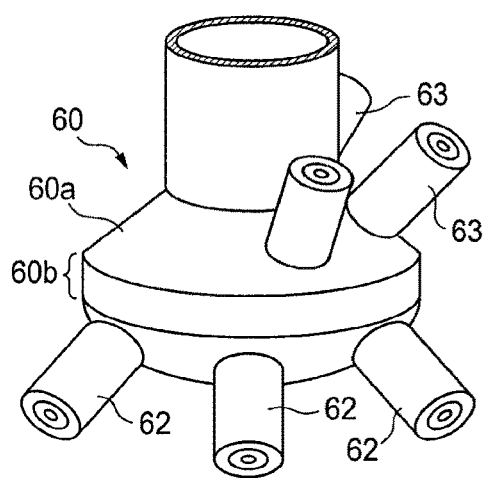
Figure 3B:
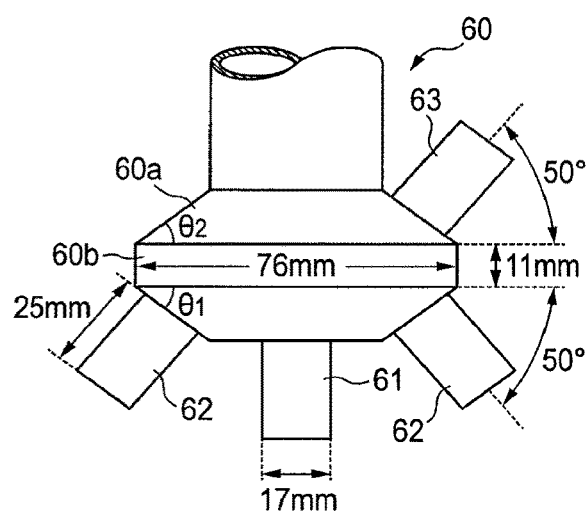
Figure 3C:
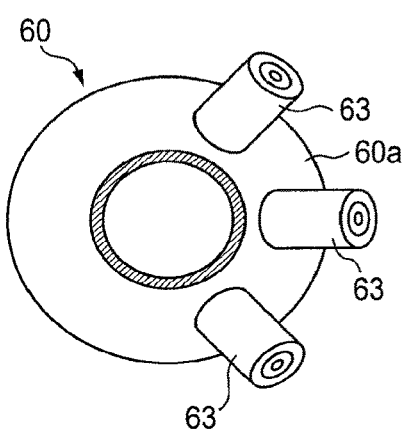
Figure 3D:
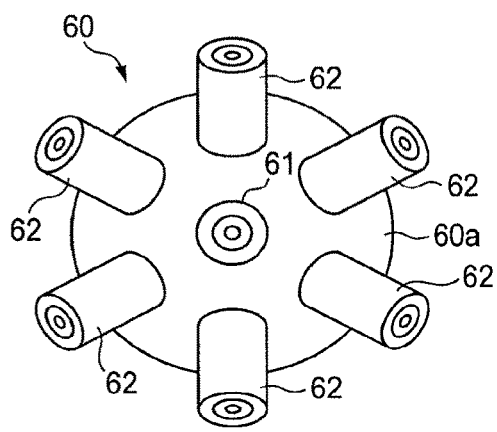

FIG. 2A is a vertical cross-sectional view showing an example of a configuration of a top cover and an upper tube plate portion of a vertical shell and tube type heat exchanger that is used in the present invention; and FIG. 2B is a horizontal cross-sectional view along a B-B line of FIG. 2A.

FIG. 2A and FIG. 2B merely show an example of the heat exchanger that may be adopted in the present invention, and the present invention is by no means limited to one shown in FIG. 2A and FIG. 2B. For example, a configuration shown in FIG. 5A and FIG. 5B as described later and other configurations can also be adopted.

In the production method of an α-olefin low polymer according to the present invention, the gas of the raw material α-olefin, such as ethylene, etc., within the reactor 10 and/or the gas component in the gas phase part of the reactor as evaporated from the liquid phase within the reactor is cooled and condensed by the heat exchanger (cooling condenser) 16a, and the formed condensed liquid is circulated and supplied into the reactor 10, thereby achieving the removal of polymerization heat generated by the low polymerization reaction.

In the heat exchanger 16a, in order to clean the upper tube plate surface within the heat exchanger 16a, preferably a circulation solvent from the column bottom of the hexene separation column 50, a circulation liquid of the condensed liquid generated in the heat exchanger 16a, or a liquefied α-olefin, etc. is supplied into the interior of the heat exchanger 16a via one or more pipings 2f through later described spray nozzles (jet nozzles) instilled in the tip of the piping 2f.

A material that constitutes the heat exchanger 16a is not particularly limited, and examples thereof include those known as a material constituting a usual reflux condenser, for example, carbon steels, copper, titanium alloys, SUS304, SUS316, SUS316L, etc., or combinations thereof. These materials are properly selected according to a process. As an example of the combination of materials, there is exemplified the case where a latter described shell side is constituted of carbon steel, whereas a tube side is constituted of SUS304. A heat transfer area of the heat exchanger 16a is properly determined according to a degree of heat removal load, a mode of load control, or the like.

In the present invention, a vertical shell and tube type heat exchanger is used as the heat exchanger 16a. For example, as shown in FIG. 2A, this vertical shell and tube type heat exchanger includes an upper tube plate 103, tubes 104, and a top cover 100 that covers the surface of the upper tube plate 103. It is preferred that the top cover 100 includes a gas supply nozzle 102 in a gas inlet for the purpose of supplying the gas withdrawn from the gas phase part of the reactor 100 in the upper center (top) of the top cover 100. It is preferred that the heat exchanger has a circular cross section in the gas circulation direction.

An inside diameter of the upper tube plate 103 (length corresponding to R in FIG. 2A) is typically 100 to 3,000 mm, and preferably 500 to 2,000 mm.

In the present embodiment, the top cover 100 includes a cylindrical part 100a and a dome part 100b of an upper part thereof, and an overall height $H_1$ of the central part (gas inlet portion) is typically 50 to 3,000 mm, and preferably 200 to 2,000 mm, whereby a height $H_2$ of the cylindrical part 100a as the peripheral part is typically 0 to 2,000 mm, and preferably 0 to 1,500 mm.

In addition, an inside diameter r of the gas supply nozzle 102 is typically 10 to 900 mm, and preferably 50 to 600 mm; a length L is typically 20 to 2,700 mm, and preferably 100 to 1,800 mm; and a ratio of the length L to the inside diameter r is typically 1 to 5 times, and preferably 1 to 3 times.

In FIG. 2A, though the upper end surfaces of the tubes 104 and the upper surface of the upper tube plate 103 are substantially flush with each other, there is also a case where the upper end of the tube 104 is protruded from the upper surface of upper tube plate 103. In this case, though a protruded length of the tube 104 from the upper tube plate 103 is typically about 3 mm, in order to make the retention amount of the catalyst-containing mist on the surface of the upper tube plate 103 small, the protruded length is preferably 1 mm or less.

In addition, as shown in FIGS. 2(a) and 2(b), in the top cover 100 of this heat exchanger, plural spray nozzle sets 60 (six sets in the present embodiment) are inserted into a gas reception chamber 105 between the top cover 100 and the upper tube plate 103.

On the upper surface of the upper tube plate 103 of the heat exchanger, since the catalyst-containing reaction liquid mist (hereinafter also referred to as "catalyst-containing mist") which has been entrained together with the supply gas from the reactor 10 retains, a polymer is formed on the upper surface of the upper tube plate 103 to plug the upper end sides of the tubes 104. In consequence, in order that the catalyst-containing mist may not retain on the upper surface of the upper tube plate 103, atomized droplets are sprayed on the tube plate surface via the spray nozzles (spray nozzle sets 60 in FIG. 2A and FIG. 2B) installed in the one or more pipings 2f and tips thereof.

Details of this spray nozzle set 60 are explained in Example 1 as described later.

It is preferred that the atomized droplets contain at least one component that is condensed in the heat exchanger, and examples thereof include those as atomized from a circulation solvent from the column bottom of the separation column of the α-olefin low polymer, a circulation liquid of the condensed liquid generated in the heat exchanger 16a, or a liquefied α-olefin, etc. In particular, it is preferred to use a circulation solvent from the column bottom of the separation column of the α-olefin low polymer (for example, the hexene separation column 50) from the viewpoint that it does not contain a solid, such as a polymer, etc., and that furthermore, the solvent having the raw material α-olefin dissolved therein in advance within the heat exchanger 16a can be supplied into the reactor 10.

As described latter, a density of the supply gas is preferably 20 kg/m$^3$ or more, particularly 30 kg/m$^3$ or more, and especially 40 kg/m$^3$ or more. In the case where when the droplets fly out from the spray nozzles (jet nozzles), a density of the gas atmosphere within the gas reception chamber 105 of the heat exchanger is 20 kg/m$^3$ or more, and particularly 40 kg/m$^3$ or more, a velocity vector in the spreading direction of droplets stalls due to resistance of a high-density gas, and as shown in Reference Example 1 as described later, a spray angle of the spray nozzle becomes smaller than that in an air atmosphere. In this case, in a method of spraying the atomized droplets directly toward the surface of the upper tube plate 103, an extremely large number of spray nozzles become necessary for entirely cleaning the surface of the upper tube plate 103.

Then, in the present invention, the supply gas from the gas supply nozzle 102 is supplied at a gas flow rate (inlet gas flow rate) of 1 m/s or more, and preferably 2 m/s or more toward the upper tube plate 103 (or the impact plate) of the heat exchanger, and this supply gas is brought into contact with the atomized droplets from the spray nozzles (jet nozzles) within the gas reception chamber 105 and then allowed to reach the surface of the upper tube plate 103, thereby preventing retention of the catalyst-containing mist on the upper tube plate 103 from occurring.

Though an upper limit of the above-described inlet gas flow rate is not particularly limited, it is typically 50 m/s or less, and preferably 30 m/s or less. This inlet gas flow rate can be controlled by a supply amount of the above-described supply gas.

In the present invention, as for the reason why the retention of the catalyst-containing mist on the upper tube plate can be prevented from occurring, the following two may be considered.

(1) The catalyst-containing mist is taken in the atomized droplets, goes through the tubes of the heat exchanger together with the atomized droplets, and flows out as the condensed liquid.

(2) The atomized droplets spread on the entirety of the upper tube plate surface together with the high-density supply gas and wash away the catalyst-containing mist attached onto the upper tube plate surface.

In the light of the above, in the present invention, the retention of the catalyst-containing mist on the upper tube plate surface is prevented from occurring to suppress the formation of a polymer by the retained catalyst, and hence, a stable operation can be continuously performed over a long period of time.

In view of the fact that the atomized droplets sprayed from the spray nozzles fall, the atomized droplets can be allowed to reach the upper tube plate surface. In the present invention, by subjecting the gas of the gas phase part within the reactor to be supplied into the heat exchanger to gas-liquid contact with the atomized droplets from the spray nozzles to allow them to go with the gas flow, the atomized droplets can be made easy to reach the entirety of the upper tube plate surface. As the spray pattern (spray configuration) of the spray nozzles, full cone, hollow cone, flat, solid and the like are exemplified and may be used in combination. In the present invention, it is preferred to use a full cone spray nozzle since mist-like liquid can be supplied onto surface of large-area at one time.

As described previously, there is a case where in the heat exchanger, an impact plate (baffle plate) is provided in the reception chamber of the gas to be condensed. In the present invention, in order to prevent the attachment of the catalyst-containing mist onto a side wall within the gas reception chamber 105 from occurring, it is preferred that an impact plate (baffle plate) is not provided in the inlet part of the supply gas.

Though the spray nozzles can also be installed within the piping 2a from the reactor 10 to the heat exchanger, it is preferred to install the spray nozzles within the top cover of the heat exchanger. In the case of installing the spray nozzles within the top cover of the heat exchanger, in order that the atomized droplets from the spray nozzles may readily come into contact with the above-described supply gas, it is preferred to provide the spray nozzles in such a manner that the direction of a part of the spray nozzles is not vertical but inclined against the upper tube plate surface so as to be directed toward the horizontal direction to the gas supply nozzle direction (toward the supply gas inlet side). That is, it is preferred to allow the direction of the spray nozzle to fall within the range of from the horizontal direction to the obliquely upward direction toward the central axis of the top cover. The horizontal direction includes not only the completely horizontal direction but also the approximately horizontal direction close to the horizontal direction (not parallel to the upper tube plate surface but within the range of an angle of preferably from 0° to ±5° against the upper tube plate surface). By inclining the spray nozzles in this way, it becomes easy to allow the atomized droplets to go with the gas flow of the supply gas. The number of spray nozzles to be inclined in the horizontal direction to the gas supply nozzle direction toward the supply gas is typically 1 or more, preferably 3 or more, and still more preferably 6 or more. Though an upper limit thereof is not particularly limited, it is typically 500 or less, and preferably 100 or less.

An spray angle of the spray nozzle such as a full cone spray nozzle is an angle at which a liquid sprayed from one spray nozzle spreads, and it is typically 15° to 170°, preferably 20' to 160°, more preferably 25° to 150°, and particularly preferably 30° to 140°. When the spray angle is larger than the lower limit value, a spread of the sprayed droplets becomes larger, a larger amount of droplets is supplied over the entirety of the tube plate surface, and the cleaning efficiency of the tube plate surface is more improved, and hence, such is preferred. In addition, when the spray angle is smaller than the upper limit value, collision of droplets from neighborhood spray nozzles becomes smaller, and a spread of the sprayed droplets becomes hardly small, and hence, such is preferred.

The number of installation places of the spray nozzles is regulated to 5 or more per 1.00 m² of an area of the upper tube plate. In the case of providing spray nozzle sets as described later, the installation places of the spray nozzles refer to not the installation places of spray nozzle sets but a sum total of the installation places of spray nozzles of each spray nozzle set. In addition, the number of spray nozzles is preferably 5 to 1,000 per m², more preferably 6 to 500 per m², and still more preferably 6 to 200 per m², with respect to an area of the upper tube plate.

In addition, it is preferred to install the spray nozzles at appropriate spaces in a circumferential or approximately circumferential state centering on the gas supply nozzle. A distance from the lower end of the spray nozzle to the upper tube plate is typically 30 to 2,500 mm, and preferably 100 to 1,500 mm.

In the present invention, a density of the supply gas that is supplied into the heat exchanger 16a is 20 kg/m³ or more, preferably 20 to 200 kg/m³, more preferably 30 to 150 kg/m³, and still more preferably 40 to 120 kg/m³.

The gas density correlates with an ethylene partial pressure, and when the ethylene partial pressure is too low, the catalytic activity and the reaction selectivity of the desired product are lowered, whereas when the ethylene partial pressure is too high, an instrument purchase cost tends to become high.

A density of the supply liquid that is supplied from the spray nozzle for the purpose of forming atomized droplets is typically 200 to 1,600 kg/m³, preferably 250 to 1,000 kg/m', and more preferably 300 to 800 kg/m³.

When the density of the supply liquid is the foregoing lower limit or more, the droplets are readily separated from the gas, and the droplets readily fall on the upper tube plate surface, and hence, cleaning of the upper tube plate surface becomes more sufficient. When the density of the supply liquid is the foregoing upper limit or less, the droplets readily go with the gas flow, and hence, the droplets can be efficiently dispersed.

In addition, a supply amount of this supply liquid (atomized droplets) is typically 0.1% to 200%, preferably 0.5% to 100%, and more preferably 1% to 50% on a weight basis relative to the supply gas amount. When the supply amount of the supply liquid is the foregoing lower limit or more, cleaning of the upper tube plate surface becomes more sufficient, whereas when the supply amount of the supply liquid is the foregoing upper limit or less, the circulation amount of the supply liquid becomes appropriate, and such is preferred from the viewpoint of economy.

The atomized droplet from the spray nozzle is typically 3 mm or less, preferably 2 mm or less, and more preferably 1 mm or less in terms of a Sauter mean diameter. Meanwhile, though a lower limit thereof is not particularly limited, from the practical standpoint, it is typically 5 μm or more, and preferably 10 μm or more in terms of a Sauter mean diameter. When the droplet diameter is too large, the number of droplets becomes small, and there is a tendency that the droplets cannot be dispersed uniformly and densely on the upper tube plate surface. In addition, the catalyst-containing mist is hardly captured by the spray droplets, and therefore, there is a tendency that an effect for preventing the retention of the catalyst-containing mist on the upper tube plate surface becomes low.

Here, as for the droplet diameter, the distribution of the spray droplet diameter can be, for example, measured on a real-time basis by using a laser analysis system, manufactured by Malvern Instruments Ltd. (product name: Spraytec). In the case where the supply liquid is an organic solvent, the droplet diameter distribution has only to be measured with water, thereby collecting the measured value with a physical properties value ratio of the organic solvent relative to water. Specifically, the droplet diameter of water may be multiplied by a 0.25 power of the ratio in surface tension, a 0.25 power of the ratio in viscosity, and a −0.25 power of the density. As the surface tension and the viscosity of the liquid are smaller, and the density of the liquid is larger, the droplet diameter becomes smaller.

A ratio of the inside diameter of the gas supply nozzle to the inside diameter R of the upper tube plate 103 of the heat exchanger ((inside diameter of the gas supply nozzle)/(inside diameter of the upper tube plate surface)) is typically 0.04 or more and 0.60 or less, preferably 0.06 or more and 0.50 or less, more preferably 0.08 or more and 0.40 or less, and still more preferably 0.10 or more and 0.35 or less. By allowing the ratio to fall within the foregoing range, the atomized droplets can be thoroughly attached onto the upper tube plate surface.

When this ratio is too small, a pressure loss on the gas supply nozzle side becomes large; a pump for returning the condensed liquid into the reactor becomes essential; and an electric bill of the compressor for circulating the non-condensable gas into the reactor increases. Conversely, when this ratio is too large, in the case where the spray nozzles are present only within the top cover, the gas flow rate within the gas reception chamber 105 is slow, and furthermore, a gas flow flux is thick, and therefore, the droplets from the spray nozzle do not thoroughly come into the interior of the gas flow flux, and there is a tendency that the droplets hardly reach the upper tube plate surface.

Though a temperature of the supply liquid is not particularly limited so long as the supply liquid is in a liquid state, it is preferred to set the temperature to a swelling temperature of the attached polymer or higher such that a jet part of the spray nozzle is hardly plugged. In the case where the attached polymer is polyethylene, the temperature of the supply liquid is preferably 100 to 200° C., and more preferably 110 to 150° C.

Other configurations of the vertical shell and tube type heat exchanger that is used as the heat exchanger 16*a* are the same as those in the conventional shell and tube type heat exchanger shown in FIG. 11. The condensed liquid from the takeout port 96*a* of a condensed liquid in FIG. 11 is returned into the reactor 10 via the pipings 2*b* and 2*d*, and the non-condensable gas (containing a part of the condensed liquid) is introduced into the gas-liquid separator 20*a* via the piping 2*c*.

As for the operation conditions of the reactor 10, a reaction temperature (actually measured value of the liquid phase temperature) is typically 50° C. to 250° C., preferably 100° C. to 200° C., and more preferably 120° C. to 170° C. In addition, a reaction pressure is in the range of typically from 1.0 to 25 MPa, preferably from 2.0 to 15 MPa, and more preferably from 3.0 to 10 MPa in terms of a gauge pressure.

Though a retention time within the reactor 10 is not particularly limited, it is in the range of typically from 1 minute to 10 hours, preferably from 3 minutes to 3 hours, and more preferably from 5 minutes to 40 minutes.

The reaction mode of the present invention is preferably a continuous mode.

It is preferred to undergo the trimerization reaction of ethylene in such a manner that a molar ratio of 1-hexene to ethylene in the reaction liquid within the reactor 10 [(molar concentration of 1-hexene in the reaction liquid)/(molar concentration of ethylene in the reaction liquid)] is preferably 0.05 to 1.5, and particularly preferably 0.10 to 1.0.

In consequence, in the case of a continuous reaction, it is preferred to adjust the catalyst concentration, the reaction pressure, or other conditions such that the molar ratio between ethylene and 1-hexene in the reaction liquid falls within the foregoing range. In this way, by production of a component having a higher boiling point than 1-hexene is suppressed, and there is a tendency that the selectivity of 1-hexene is more increased.

In addition, a linear gas velocity of the gas phase part within the reactor 10 is preferably 0.1 cm/s to 10.0 cm/s, more preferably 0.3 cm/s to 5.0 cm/s, and still more preferably 0.5 cm/s to 3.0 cm/s.

By controlling the linear gas velocity of the gas phase part of the reactor 10 within the foregoing range, on the occasion of sending the ethylene gas within the reactor 10 and the vapor component evaporated from the liquid phase to the heat exchanger 16*a*, there is a tendency that the entrainment of the reaction liquid is suppressed.

An outlet temperature of the gas of the gas phase part of the reactor is lower by preferably 8° C. or more, more preferably 10° C. or more, still more preferably 10 to 40° C., and particularly preferably 15 to 35° C. than the liquid phase temperature of the reactor 10.

In view of the fact that the outlet temperature of the gas of the gas phase part of the reactor is lower by 8° C. or more than the liquid phase temperature, since a condensed liquid is generated from the gas of the gas phase part while using a mist of the reaction liquid as a nucleus, the mist diameter becomes large, the gas-liquid separator can be readily achieved in the gas phase part of the reaction, and there is a tendency that the number of mists of the reaction liquid in the outlet gas of the gas phase part of the reactor decreases.

However, it is not necessary to make the outlet temperature of the gas of the gas phase part of the reactor excessively low. The reason for this resides in the matter that it is necessary to increase the cooling heat transfer surface of the heat exchanger 16*a* and/or to change the coolant from water to a liquefied evaporative coolant or the like, leading to an increase of construction costs.

The reaction product liquid which has reached a predetermined conversion rate in the reactor 10 is continuously withdrawn from the bottom of the reactor 10 via a piping 11 and supplied into the degassing tank 20. At that time, the trimerization reaction of ethylene is stopped with a catalyst deactivator, such as 2-ethylhexanol, etc., as supplied from a deactivator supply pipe 11*a*. The unreacted ethylene degassed in the degassing tank 20 is circulated and supplied into the reactor 10 from the upper part of the degassing tank 20 via the heat exchanger (condenser) 16, the circulating piping 21, the compressor 17, and the first supply pipe 12.

In addition, the reaction product liquid from which the unreacted ethylene has been degassed is withdrawn from the tank bottom of the degassing tank 20.

As for the operation conditions of the degassing tank 20, a temperature is typically 40° C. to 240° C., and preferably 90° C. to 190° C., and a pressure is typically 0 to 15 MPa, and preferably 0.5 to 9 MPa in terms of a gauge pressure.

The reaction product liquid withdrawn from the tank bottom of the degassing tank 20 goes through a piping 22 and is supplied into the ethylene separation column 30. In the ethylene separation column 30, ethylene is distilled and separated from the column top by means of distillation, and this ethylene is circulated and supplied into the reactor 10 via the circulating piping 31 and the first supply pipe 12. In addition, the reaction product liquid from which ethylene has been removed is withdrawn from the column bottom.

As for the operation conditions of the ethylene separation column 30, a column top pressure is typically 0 to 3 MPa, and preferably 0.1 to 2 MPa in terms of a gauge pressure; a reflux ratio (R/D) is typically 0 to 500, and preferably 0.1 to 100; and a necessary number of theoretical plate is typically 2 to 20 plates.

The reaction product liquid from which ethylene has been distilled and separated in the ethylene separation column 30 is withdrawn from the column bottom of the ethylene separation column 30 is supplied into the high boiling separation column 40 via a piping 32. In the high boiling separation column 40, a high boiling point component (HB: high boiler) is withdrawn from the column bottom via a piping 42 by means of distillation. In addition, a distillate from which the high boiling point component has been separated is withdrawn from the column top via a piping 41.

As for the operation conditions of the high boiling separation column 40, a column top pressure is typically 0 to 1 MPa, and preferably 0 to 0.5 MPa in terms of a gauge pressure; a reflux ratio (R/D) is typically 0 to 100, and preferably 0.1 to 20; and a necessary number of theoretical plate is typically 3 to 50 plates.

Subsequently, the distillate withdrawn from the column top of the high boiling separation column 40 is supplied into the hexene separation column 50 via a piping 41. In the hexene separation column 50, 1-hexene is distilled out from the column top via a piping 51 by means of distillation.

In addition, the reaction solvent, for example, n-heptane, is withdrawn from the column bottom of the hexene separation column 50 and circulated and supplied as a reaction solvent into the reactor 10 via a solvent circulation piping 52, a pump 13c, and the second supply pipe 13.

As for the operation conditions of the hexene separation column 50, a pressure of the column top is typically 0 to 1 MPa, and preferably 0 to 0.5 MPa; a reflux ratio (RID) is typically 0 to 100, and preferably 0.1 to 20; and a necessary number of theoretical plate is typically 5 to 100 plates.

[α-Olefin]

In the production method of an α-olefin according to the present invention, examples of the α-olefin that is used as a raw material include substituted or unsubstituted α-olefins having 2 to 30 carbon atoms, preferably 2 to 8 carbon atoms, and more preferably 2 to 4 carbon atoms. Specific examples of such an α-olefin include ethylene, propylene, 1-butene, 1-hexene, 1-octene, 3-methyl-1-butene, 4-methyl-1-pentene, and the like. Above all, ethylene is preferred as the raw material α-olefin in the present invention.

In the case of using ethylene as the raw material, the raw material may contain an impurity component other than ethylene. Specifically, examples of the impurity component include methane, ethane, nitrogen, oxygen, water, acetylene, carbon dioxide, carbon monoxide, hydrogen sulfide, and the like.

With respect to methane, ethane, and nitrogen, though there is no particular limitation, the content thereof is preferably 0.1 mol % or less relative to the raw material ethylene. With respective to oxygen, water, acetylene, carbon dioxide, carbon monoxide or a sulfur component, such as hydrogen sulfide, etc., the content thereof is preferably 1 mol ppm or less relative to the raw material ethylene.

[Catalyst]

Though the catalyst that is used in the present invention is not particularly limited so long as it is able to subject the raw material α-olefin to low polymerization reaction to form an α-olefin low polymer, those containing, as constituent components of the catalyst, a transition metal-containing compound, a nitrogen-containing compound, and an aluminum-containing compound are preferred. In addition, from the viewpoint of improving the catalytic activity and the selectivity of the desired α-olefin low polymer, it is more preferred that the catalyst contains a halogen-containing compound as the constituent component.

<Transition Metal-Containing Compound>

Though a metal that is contained in the transition metal-containing compound that is preferably used as the constituent unit of the catalyst of the present invention is not particularly limited so long as it is a transition metal, above all, a transition metal belonging to Groups 4 to 6 of the Periodic Table is preferably used.

Specifically, at least one metal selected from the group consisting of chromium, titanium, zirconium, vanadium, and hafnium is preferred, chromium or titanium is more preferred, and chromium is most preferred.

The transition metal-containing compound is typically at least one compound represented by a general formula: $MeZ_n$. Here, in the general formula: $MeZ_n$, Me is a transition metal, and Z is an arbitrary organic group or inorganic group, or a negative atom. n represents an integer of from 1 to 6, and preferably 2 or more. In the case where n is 2 or more, each Z may be the same as or different from every other Z.

As the organic group, there is exemplified an optionally substituted hydrocarbon group having 1 to 30 carbon atoms. Specifically, examples thereof include a carbonyl group, an alkoxy group, a carboxyl group, a β-diketonate group, a β-ketocarboxyl group, a β-ketoester group, an amide group, and the like.

In addition, examples of the inorganic group include metal salt-forming groups, such as a nitric acid group, a sulfuric acid group, etc. In addition, examples of the negative atom include oxygen, a halogen, and the like. The transition metal-containing compound in which a halogen is contained is not included in a halogen-containing compound as described later.

In the case of the transition metal-containing compound in which the transition metal is chromium (hereinafter sometimes referred to as "chromium-containing compound"), specific examples thereof include chromium(IV)-tert-butoxide, chromium(III) acetyl acetonate, chromium(III) trifluoroacetyl acetonate, chromium(III) hexafluoroacetyl acetonate, chromium(III) (2,2,6,6-tetramethyl-3,5-heptanedionate), $Cr(PhCOCHCOPh)_3$ (wherein Ph represents a phenyl group), chromium(II) acetate, chromium (III) acetate, chromium(III) 2-ethylhexanoate, chromium (III) benzoate, chromium(III) naphthenate, chromium(III) heptanoate, $Cr(CH_3COCHCOOCH_3)_3$, chromous chloride, chromic chloride, chromous bromide, chromic bromide, chromous iodide, chromic iodide, chromous fluoride, chromic fluoride, and the like.

In the case of the transition metal-containing compound in which the transition metal is titanium (hereinafter sometimes referred to as "titanium-containing compound"), specific examples thereof include $TiCl_4$, $TiBr_4$, $TiI_4$, $TiBrCl_3$, $TiBr_2Cl_2$, $Ti(OC_2H_5)_4$, $Ti(OC_2H_5)_2Cl_2$, $Ti(O-n-C_3H_7)_4$, $Ti(O-n-C_3H_7)_2Cl_2$, $Ti(O-iso-C_3H_7)_4$, $Ti(O-iso-C_3H_7)_2Cl_2$, $Ti(O-n-C_4H_9)_4$, $Ti(O-n-C_4H_9)_2Cl_2$, $Ti(O-iso-C_4H_9)_4$, $Ti(O-iso-C_4H_9)_2Cl_2$, $Ti(O-tert-C_4H_9)_4$, $Ti(O-tert-C_4H_9)_2Cl_2$, $TiCl_4(thf)_2$ (wherein thf represents tetrahydrofuran), $Ti[(CH_3)_2N]_4$, $Ti[(C_2H_5)_2N]_4$, $Ti[(n-C_3H_7)_2N]_4$, $Ti[(iso-C_3H_7)_2N]_4$, $Ti[(n-C_4H_9)_2N]_4$, $Ti[(tert-C_4H_9)_2N]_4$, $Ti(OSO_3CH_3)_4$, $Ti(OSO_3C_2H_5)_4$, $Ti(OSO_3C_3H_7)_4$, $Ti(OSO_3C_4H_9)_4$, $TiCp_2Cl_2$, $TiCp_2C_1Br$ (wherein Cp represents a cyclopentadienyl group; hereinafter the same in the zirconium-containing compound), $Ti(OCOC_2H_5)_4$, $Ti(OCOC_2H_5)_2Cl_2$, $Ti(OCOC_3H_7)_4$, $Ti(OCOC_3H_7)_2Cl_2$, $Ti(OCOC_4H_9)_4$, $Ti(OCOC_4H_9)_2Cl_2$, and the like.

In the case of the transition metal-containing compound in which the transition metal is zirconium (hereinafter sometimes referred to as "zirconium-containing compound"), specific examples thereof include $ZrCl_4$, $ZrBr_4$, $ZrI_4$, $ZrBrCl_3$, $ZrBr_2Cl_2$, $Zr(OC_2H_5)_4$, $Zr(OC_2H_5)_2Cl_2$, $Zr(O-n-C_3H_7)_4$, $Zr(O-n-C_3H_7)_2Cl_2$, $Zr(O-iso-C_3H_7)_4$, $Zr(O-iso-C_3H_7)_2Cl_2$, $Zr(O-n-C_4H_9)_4$, $Zr(O-n-C_4H_9)_2Cl_2$, $Zr(O-iso-C_4H_9)_4$, $Zr(O-iso-C_4H_9)_2Cl_2$, $Zr(O-tert-C_4H_9)_4$, $Zr(O-tert-C_4H_9)_2Cl_2$, $Zr[(CH_3)_2N]_4$, $Zr[(C_2H_5)_2N]_4$, $Zr[(n-C_3H_7)_2N]_4$, $Zr[(iso-C_3H_7)_2N]_4$, $Zr[(n-C_4H_9)_2N]_4$, $Zr[(tert-C_4H_9)_2N]_4$, $Zr(OSO_3CH_3)_4$, $Zr(OSO_3C_2H_5)_4$, $Zr(OSO_3C_3H_7)_4$, $Zr(OSO_3C_4H_9)_4$, $ZrCp_2Cl_2$, $ZrCp_2C_1Br$, $Zr(OCOC_2H_5)_4$, $Zr(OCOC_2H_5)_2Cl_2$, $Zr(OCOC_3H_7)_4$, $Zr(OCOC_3H_7)_2Cl_2$, $Zr(OCOC_3H_7)_4$, $Zr(OCOC_3H_7)_2Cl_2$, $Zr(OCOC_4H_9)_4$, $Zr(OCOC_4H_9)_2Cl_2$, $ZrCl_2(HCOCFCOF)_2$, $ZrCl_2(CH_3COCFCOCH_3)_2$, and the like.

In the case of the transition metal-containing compound in which the transition metal is hafnium (hereinafter sometimes referred to as "hafnium-containing compound"), specific examples thereof include dimethylsilylenebis{1-(2-methyl-4-isopropyl-4H-azulenyl)}hafnium dichloride, dimethylsilylenebis{1-(2-methyl-4-phenyl-4H-azulenyl)}hafnium dichloride, dimethylsilylenebis[1-{2-methyl-4-(4-chlorophenyl)-4H-azulenyl}]hafnium dichloride, dimethylsilylenebis[1-{2-methyl-4-(4-fluorophenyl)-4H-azulenyl}]hafnium dichloride, dimethylsilylenebis[1-{2-methyl-4-(3-chlorophenyl)-4H-azulenyl}]hafnium dichloride, dimethylsilylenebis[1-{2-methyl-4-(2,6-dimethylphenyl)-4H-azulenyl}]hafnium dichloride, dimethylsilylenebis{1-(2-methyl-4,6-diisopropyl-4H-azulenyl)}hafnium dichloride, diphenylsilylenebis{1-(2-methyl-4-phenyl-4H-azulenyl)}hafnium dichloride, methylphenylsilylenebis{1-(2-methyl-4-phenyl-4H-azulenyl)}hafnium dichloride, methylphenylsilylenebis[1-{2-methyl-4-(1-naphthyl)-4H-azulenyl}]hafnium dichloride, dimethylsilylenebis{1-(2-ethyl-4-phenyl-4H-azulenyl)}hafnium dichloride, dimethylsilylenebis[1-{2-ethyl-4-(1-anthracenyl)-4H-azulenyl}] hafnium dichloride, dimethylsilylenebis[1-{2-ethyl-4-(2-anthracenyl)-4H-azulenyl}]hafnium dichloride, dimethylsilylenebis[1-{2-ethyl-4-(9-phenanthryl)-4H-azulenyl}]hafnium dichloride, dimethylsilylenebis[1-{2-methyl-4-(4-biphenylyl)-4H-azulenyl}]hafnium dichloride, dimethylgermirenebis[1-{2-methyl-4-(4-biphenylyl)-4H-azulenyl}]hafnium dichloride, dimethylsilylenebis[1-{2-ethyl-4-(3,5-dimethyl-4-trimethylsilylphenyl)-4H-azulenyl}]hafnium dichloride, dimethylsilylene[1-{2-methyl-4-(4-biphenylyl)-4H-azulenyl}][1-{2-methyl-4-(4-biphenylyl)indenyl}]hafnium dichloride, dimethylsilylene{1-(2-ethyl-4-phenyl-4H-azulenyl)}{1-(2-methyl-4,5-benzoindenyl}}hafnium dichloride, dimethylsilylenebis{1-(2-methyl-4-phenylindenyl)}hafnium dichloride, dimethylsilylenebis{1-(2-methyl-4,5-benzoindenyl)}hafnium dichloride, dimethylsilylenebis[1-{2-methyl-4-(1-naphthyl) indenyl)}hafnium dichloride, and the like.

These transition metal-containing compounds may be used alone or may be used in combination of two or more thereof. Of those transition metal-containing compounds, chromium-containing compounds are preferred; and of the chromium-containing compounds, chromium(III) 2-ethylhexanoate is particularly preferred.

<Nitrogen-Containing Compound>

Though the nitrogen-containing compound that is preferably used as the constituent component of the catalyst in the present invention is not particularly limited, examples thereof include amines, amides, imides, and the like.

Examples of the amine include pyrrole compounds. Specific examples thereof include pyrroles, such as pyrrole, 2,4-dimethylpyrrole, 2,5-dimethylpyrrole, 2,5-diethylpyrrole, 2,4-diethylpyrrole, 2,5-di-n-propylpyrrole, 2,5-di-n-butylpyrrole, 2,5-di-n-pentylpyrrole, 2,5-di-n-hexylpyrrole, 2,5-benzylpyrrole, 2,5-diisopropylpyrrole, 2-methyl-5-ethylpyrrole, 2,5-dimethyl-3-ethylpyrrole, 3,4-dimethylpyrrole, 3,4-dichloropyrrole, 2,3,4,5-tetrachloropyrrole, 2-acetylpyrrole, indole, 2-methylindole, a dipyrrole in which two pyrrole rings are bonded to each other via a substituent, etc., and derivatives thereof.

Examples of the derivative include metal pyrrolide derivatives. Specific examples thereof include aluminum pyrrolides, such as diethylaluminum pyrrolide, ethylaluminum dipyrrolide, aluminum tripyrrolide, diethylaluminum (2,5-dimethylpyrrolide), ethylaluminum bis(2,5-dimethylpyrrolide), aluminum tris(2,5-dimethylpyrrolide), diethylaluminum (2,5-diethylpyrrolide), ethylaluminum bis(2,5-diethylpyrrolide), aluminum tris(2,5-diethylpyrrolide), etc.; sodium pyrrolides, such as sodium pyrrolide, sodium (2,5-dimethyl-pyrrolide), etc.; lithium pyrrolides, such as lithium pyrrolide, lithium 2,5-dimethylpyrrolide), etc.; and potassium pyrrolides, such as potassium pyrrolide, potassium (2,5-dimethylpyrrolide), etc.

The aluminum pyrrolide is not included in an aluminum-containing compound as described later. In addition, the pyrrole compound containing a halogen is not included in a halogen-containing compound as described later.

In addition, diphosphinoamines, such as bis(diethylphosphino-ethyl)amine, bis(diphenylphosphino-ethyl)amine, N,N-bis(diphenylphosphino)methylamine, or N,N-bis(diphenylphosphino)isopropylamine, may also be useful as the amine.

Examples of the amide include acetamide, N-methylhexanamide, succinamide, maleamide, N-methylbenzamide, imidazole-2-carboxamide, di-2-thenoylamine, β-lactam, δ-lactam, ε-caprolactam, and salts thereof with a metal belonging to Group 1, 2, or 13 of the Periodic Table.

Examples of the imide include 1,2-cyclohexanedicarboxyimide, succinimide, phthalimide, maleimide, 2,4,6-piperidinetrione, perhydroazesine-2,10-dione, and salts thereof with a metal belonging to Group 1, 2, or 13 of the Periodic Table.

Examples of the sulfonamide or sulfonimide include benzene sulfonamide, N-methylmethane sulfonamide, N-methyltrifluoromethyl sulfonamide, and salts thereof with a metal belonging to Group 1, 2, or 13 of the Periodic Table.

These nitrogen-containing compounds may be used alone or may be used in combination of two or more thereof.

In the present invention, of those, amines are preferred, and above all, pyrrole compounds are more preferred, and 2,5-dimethylpyrrole or diethylaluminum (2,5-dimethylpyrrolide) is particularly preferred.

<Aluminum-Containing Compound>

Though the aluminum-containing compound that is preferably used as the catalyst component of the present invention is not particularly limited, examples thereof include a trialkylaluminum compound, an alkoxyalkylaluminum compound, a hydrogenated alkylaluminum compound, an aluminoxane compound, and the like. Here, the carbon number of each of the alkyl and the alkoxy is typically 1 to 20, and preferably 1 to 4.

It should be construed that a halogenated alkylaluminum compound is not included in the aluminum-containing compound but included in a halogen-containing compound as described later.

Examples of the trialkylaluminum compound include trimethylaluminum, triethylaluminum, and triisobutylaluminum. Examples of the alkoxyalkylaluminum compound include diethylaluminum ethoxide.

Examples of the hydrogenated alkylaluminum compound include diethylaluminum hydride. Examples of the aluminoxane compound include methylaluminoxane and ethylaluminoxane.

These aluminum-containing compounds may be used alone or may be used in combination of two or more thereof. Of those, a trialkylaluminum compound is preferred, and triethylaluminum is more preferred.

<Halogen-Containing Compound>

It is preferred that the catalyst of the present invention further contains a halogen-containing compound as the constituent component in addition to the above-described components. Though this halogen-containing compound is not particularly limited, examples thereof include a halogenated alkylaluminum compound, a benzyl chloride skeleton-containing compound, a linear halogenated hydrocarbon having two or more halogen atoms and having 1 or more carbon atoms, and a cyclic halogenated hydrocarbon having one or more halogen atoms and having 3 or more carbon atoms.

Examples of the halogen-containing compound include a halogenated alkylaluminum-containing compound, such as diethylaluminum monochloride, ethylaluminum sesquichloride, ethylaluminum dichloride, etc., benzyl chloride, 1-(chloroethyl)benzene, 2-methylbenzyl chloride, 3-methylbenzyl chloride, 4-methylbenzyl chloride, 4-ethylbenzyl chloride, 4-isopropylbenzyl chloride, 4-tert-butylbenzyl chloride, 4-vinylbenzyl chloride, α-ethyl-4-methylbenzyl chloride, α,α'-dichloro-o-xylene, α,α'-dichloro-m-xylene, α,α'-dichloro-p-xylene, 2,4-dimethylbenzyl chloride, 2,5-dimethylbenzyl chloride, 2,6-dimethylbenzyl chloride, 3,4-dimethylbenzyl chloride, 2,3,5,6-tetramethylbenzyl chloride, 1-(chloromethyl)naphthalene, 1-(chloromethyl)-2-methylnaphthalene, 1,4,-bis-chloromethyl-2,3-dimethylnaphthalene, 1,8-bis-chloromethyl-2,3,4,5,6,7-hexamethylnaphthalene, 9-(chloromethyl)anthracene, 9,10-bis(chloromethyl)anthracene, 7-(chloromethyl) benzanthracene, 7-chloromethyl-12-methylbenzanthracene, methylene chloride, chloroform, carbon tetrachloride, 1,1-dichloroethane, 1,2-dichloroethane, 1,1,1-trichloroethane, 1,1,2-trichloro ethane, 1,1,2,2-tetrachloro ethane, pentachloroethane, hexachloroethane, dichloroethylene, trichloroethylene, perchloroethylene, 1,2,3-trichlorocyclopropane, 1,2,3,4,5,6-hexachlorocyclohexane, 1,4-bis(trichloromethyl)-2,3,5,6-tetrachlorobenzene, and the like.

These halogen-containing compounds may be used alone or may be used in combination of two or more thereof.

<Amount of Catalyst Used>

Though a ratio of each of the constituent components of the transition metal-containing compound, the nitrogen-containing compound, the aluminum-containing compound, and the halogen-containing compound, each of which is the catalyst component that is preferably used as the catalyst in the present invention, is not particularly limited, the amount of the nitrogen-containing compound is typically 1 mol to 50 mols, and preferably 1 mol to 30 mols; and the amount of the aluminum-containing compound is typically 1 mol to 2,000 mols, and preferably 10 mols to 1,000 mols per mol of the transition metal-containing compound. In the case where the catalyst contains the halogen-containing compound, the amount of the halogen-containing compound is typically 1 mol to 150 mols, and preferably 1 mol to 100 mols per mol of the transition metal-containing compound.

In the present invention, though the amount of the catalyst used is not particularly limited, the amount as converted into a transition metal element of the transition metal-containing compound is typically $1.0 \times 10^{-9}$ mols to 0.5 mols, preferably $5.0 \times 10^{-9}$ mols to 0.2 mols, and more preferably $1.0 \times 10^{-8}$ mols to 0.05 mols per liter of a reaction solvent as described later.

By using such a catalyst, for example, in the case of using ethylene as the raw material, hexene that is a trimer of ethylene can be obtained in a selectivity of 90% or more. Furthermore, in that case, a ratio of 1-hexene occupying in the hexene can be made to 99% or more.

<Catalyst Preparation>

The catalyst that is used in the present invention preferably contains the transition metal-containing compound, the nitrogen-containing compound, and the aluminum-containing compound as the constituent components of the catalyst and more preferably further contains the halogen-containing compound as the constituent component. Though a use mode thereof is not particularly limited, when the raw material α-olefin and the catalyst are brought into contact with each other in an embodiment in which the transition metal-containing compound and the aluminum-containing compound do not previously come into contact with each other, or a previous contact time is short, the low polymerization reaction of the raw material α-olefin can be suitably selectively performed, and a low polymer of the raw material α-olefin can be obtained in a high yield, and hence, such is preferred.

The "embodiment in which the transition metal-containing compound and the aluminum-containing compound do not previously come into contact with each other, or a previous contact time is short" as referred to herein means that the above-described embodiment is maintained not only at the time of starting the reaction but also on the occasion of subsequently additionally supplying the raw material α-olefin and the respective catalyst components into the reactor. However, the above-described specified embodiment is a preferred embodiment required on the occasion of preparing the catalyst, and after the catalyst is prepared, such an embodiment is irrelevant. In consequence, in the case of recovering the already prepared catalyst from the reaction system and reusing it, the catalyst can be reused irrespective of the above-described preferred embodiment.

In the case where the catalyst contains, for example, the above-described four components, namely the transition metal-containing compound (hereinafter referred to as "catalyst component (a)"), the nitrogen-containing compound (hereinafter referred to as "catalyst component (b)"), the aluminum-containing compound (hereinafter referred to as "catalyst component (c)"), and the halogen-containing compound (hereinafter referred to as "catalyst component (d)"), examples of the contact method of the respective components include the following (1) to (10).

(1) A method of introducing the catalyst component (a) into a solution containing the catalyst components (b), (c), and (d).

(2) A method of introducing the catalyst component (c) into a solution containing the catalyst components (a), (b), and (d).

(3) A method of introducing the catalyst components (b) and (c) into a solution containing the catalyst components (a) and (d).

(4) A method of introducing the catalyst components (a) and (b) into a solution containing the catalyst components (c) and (d).

(5) A method of introducing the catalyst components (c) and (d) into a solution containing the catalyst components (a) and (b).

(6) A method of introducing the catalyst components (a) and (d) into a solution containing the catalyst components (b) and (c).

(7) A method of introducing the catalyst components (a), (b), and (d) into a solution containing the catalyst component (c).

(8) A method of introducing the catalyst components (b) to (d) into a solution containing the catalyst component (a).

(9) A method of introducing a liquid prepared by introducing the catalyst component (a) into a solution containing the catalyst components (b) and (c), and a solution containing the catalyst component (d) simultaneously and independently into the reactor (if desired, a solution containing the catalyst component (c) may be further introduced into the reactor).

(10) A method of introducing the respective catalyst components (a) to (d) simultaneously and independently into the reactor.

Each of the above-described solutions is typically prepared by using a solvent that is used for the reaction.

[Reaction Solvent]

In the production method of an α-olefin low polymer according to the present invention, the low polymerization reaction of an α-olefin is performed in a reaction solvent.

Though the reaction solvent is not particularly limited, a saturated hydrocarbon is preferably used. The reaction solvent is preferably a chain saturated hydrocarbon or an alicyclic saturated hydrocarbon each having 3 to 20 carbon atoms, such as butane, pentane, 3-methylpentane, n-hexane, n-heptane, 2-methylhexane, octane, cyclohexane, methylcyclohexane, 2,2,4-trimethylpentane, decalin, etc.

In addition, as the reaction solvent, an aromatic hydrocarbon, such as benzene, toluene, xylene, ethylbenzene, mesitylene, tetralin, etc., or an α-olefin low polymer itself, as formed by the low polymerization reaction, specifically, 1-hexene, decene, etc. as obtained on the occasion of trimerizing ethylene, can also be used. These reaction solvents may be used alone or may be used as a mixed solvent of two or more thereof.

Of those solvents, from the standpoint that the formation or attachment of a by-product polymer, such as polyethylene, etc., can be suppressed, and furthermore, from the standpoint that there is a tendency that high catalytic activity is obtained, a chain saturated hydrocarbon or an alicyclic saturated hydrocarbon each having 4 to 10 carbon atoms is preferred, and specifically, n-heptane or cyclohexane is preferred, and n-heptane is most preferred.

Though an amount of the reaction solvent used is not particularly limited, it is typically 0.5 to 5.0 times, and preferably 1.0 to 2.5 times in terms of a mass ratio relative to the supply amount of the raw material α-olefin that is supplied into the reactor.

[α-Olefin Low Polymer]

The α-olefin low polymer that is a product is an α-olefin obtained by the low polymerization reaction of an α-olefin as the raw material. The α-olefin low polymer as referred to in the present invention means an oligomer in which a several number of the above-described raw material α-olefins that are a monomer are bonded to each other. Specifically, the α-olefin low polymer is a polymer in which 2 to 10 of the above-described raw material α-olefins that are a monomer are bonded to each other. In the case of using ethylene as the raw material, 1-butene, 1-hexene, 1-octene, and 1-decene that are a low polymer (dimer to pentamer) of ethylene can be obtained. In particular, 1-hexene that is a trimer of ethylene and/or 1-octene that is a tetramer of ethylene can be obtained in a high yield and a high selectivity. 1-Hexene obtained when ethylene is selectively trimerized is preferred.

EXAMPLES

The present invention is hereunder described more specifically based on Examples. However, it should be construed that the present invention is not limited by the following Examples so long as the gist thereof is not deviated.

In the following Examples and Comparative Examples, flow simulation of droplets flying out from a spray was performed using, as a fluid analysis program, STAR-CCM+ v.7.06, manufactured by CD-adapco.

Reference Example 1

In a sealable cylindrical vessel having an upper lid and a bottom lid and having an inside diameter of 4.4 m and a height 3.3 m, one full cone type spray nozzle positioning on the central axis of the vessel and having a designed spray angle (here, the spray angle is a spray angle of the spray nozzle) of 60° was installed perpendicularly to the lower surface of the vessel in a height position of 2 m from the bottom while making an exhaust nozzle downward.

n-Heptane (liquid density: 600 kg/m$^3$) at a temperature of 115° C. was supplied at a rate of 2,000 kg/h into the full cone spray nozzle. At that time, a supply initial velocity of the droplet was 50 m/s, and a droplet diameter was 1 mm. At that time, an ethylene pressure within the vessel was changed, a gas density was adjusted to 1.2, 10, 20, and 100 kg/m$^3$, respectively, and a degree of spreading of droplets was compared. The results are shown in the following Table 1 and FIG. 9.

TABLE 1

| Gas density (kg/m$^3$) | 1.2 | 10 | 20 | 100 |
|---|---|---|---|---|
| Effective spray diameter (m) | 0.56 | 0.44 | 0.31 | 0.13 |
| Effective spray area (m$^2$) | 0.25 | 0.15 | 0.075 | 0.013 |

Figure 9:
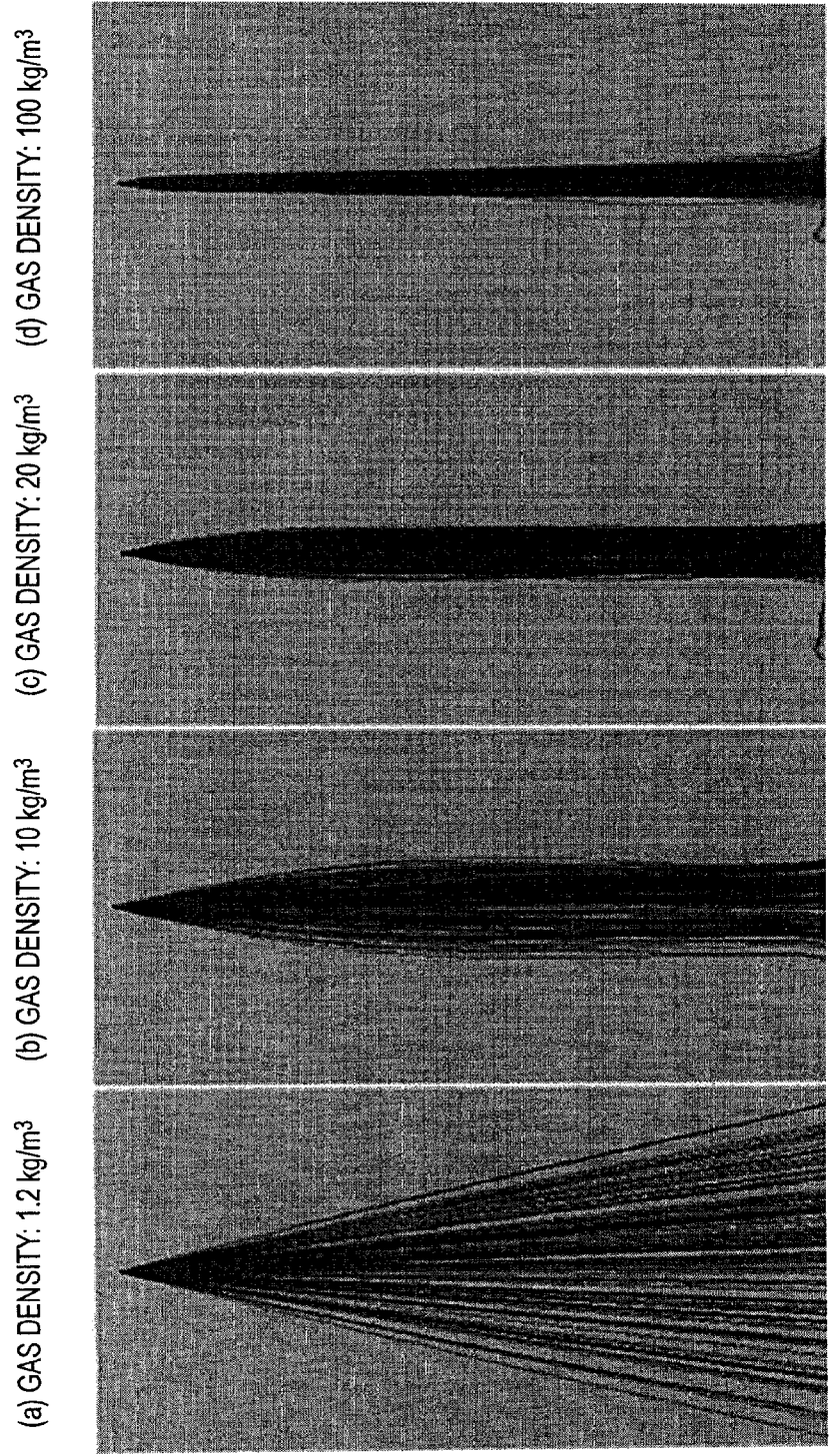
In FIG. 9, (a) to (d) are locus charts of droplets showing the results of Reference Example 1.

In Table 1, the effective spray diameter and area on the surface at a distance of 500 mm from a tip of the spray nozzle are described. In FIG. 9, (a) to (d) are locus charts of droplets of n-heptane.

From these results, it is noted that in the case where the gas density of 20 kg/m$^3$ or more, the effective spray area becomes 30% or less as compared with the case where the gas density at atmospheric pressure is 1.2 kg/m$^3$.

Example 1

In a vertical shell and tube type heat exchanger (upper tube plate area: 1.33 m$^2$) shown in FIG. 2A, all of six spray nozzle sets 60 each having ten full cone spray nozzles 61 to 63 in a nozzle body 60*a* in a disposition shown in FIG. 3A to FIG. 3D were provided, thereby installing all of the sixty full cone spray nozzles 61 to 63.

The number of spray nozzles per 1.00 m$^2$ of an area of the upper tube plate 103 was about 45.

The spray nozzles 61 to 63 of the spray nozzle set 60 are one vertically downward central nozzle 61 disposed in the center, six radially obliquely downward nozzles 62 disposed at six equal sites in the circumferential direction, and three radially obliquely upward nozzles 63. The obliquely upward nozzles 63 have an angle around the axis of 60° mutually and are provided so as to be directed toward the central axis side of the top cover 100 as shown in FIG. 2B. A depression angle of the nozzle 62 is 50° ($\theta_1$=40°), and an elevation angle of the nozzle 63 is 50° ($\theta_2$=40°).

A trunk part 60*b* of the nozzle body 60*a* has a diameter of 76 mm and a height of 11 mm, and each of the nozzles 61 to 63 has a diameter of 17 mm and a length of 25 mm.

Figure 4:
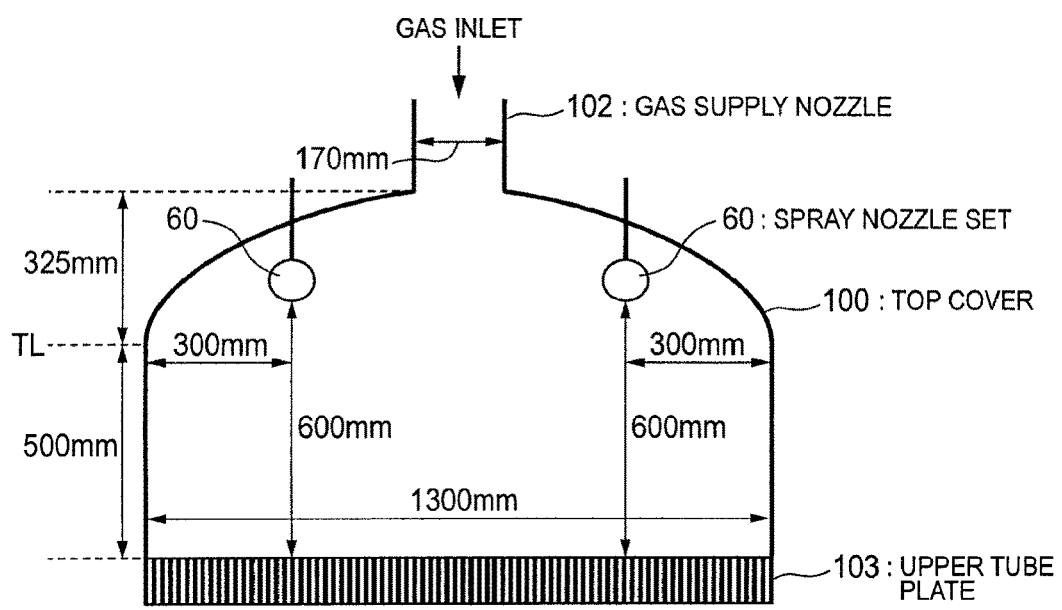
FIG. 4 is a schematic view showing dimensions of respective parts of a shell and tube type heat exchanger used in Example 1.

The instillation position of the spray nozzle set 60 and the dimensions of each of the parts of the top cover 100, the gas supply nozzle 102, and the upper tube plate 103 are shown in FIG. 4. In FIG. 4, TL (tangent line) represents a boundary portion between a cylindrical portion of the main body of the top cover 100 and a corner part of a dished head constituting the upper part of the main body.

n-Heptane (liquid density: 600 kg/m$^3$) at a temperature of 115° C. was supplied at a rate of 79 kg/h into each of the full cone spray nozzles (designed spray angle: 60°) 61 to 63 of each of the spray nozzle sets 60. A supply initial velocity of the droplet was 12 m/s, and a droplet diameter was 0.15 mm in terms of a Sauter mean diameter. In addition, a gas having a density of 92 kg/m$^3$ and composed mainly of ethylene, n-heptane, and 1-hexene was supplied at a flow rate of 706 m$^3$/h from the gas supply nozzle (inside diameter: 170 mm, length: 500 mm) 102 of the top cover 100 of the heat exchanger.

At that time, a cleaning state by n-heptane droplets on the upper surface of the upper tube plate 103 of the heat exchanger was evaluated in terms of attachment uniformity of droplets, and the results are shown in Table 2.

Figure 10A:
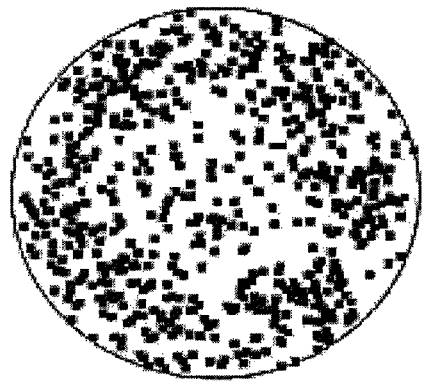
FIG. 10A and FIG. 10B are schematic views showing judgement examples of attachment uniformity of droplets onto the surface of an upper tube in Examples and Comparative Examples.
Figure 10B:
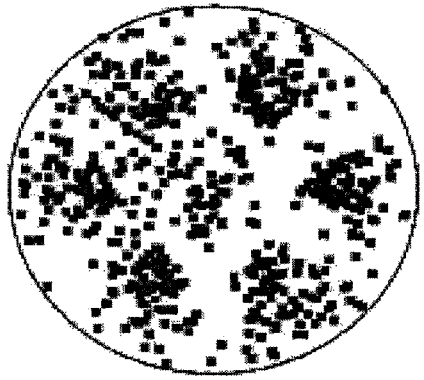

The attachment uniformity of droplets was evaluated on a judgement basis as shown in FIG. 10A and FIG. 10B. When the attachment uniformity of droplets is good (◯), the cleanability of the upper tube plate surface is excellent, but when the attachment uniformity of droplets is bad (x), the cleanability of the upper tube plate surface is poor.

Example 2

The operation was performed by the entirely same method as in Example 1, except for changing the droplet diameter (Sauter mean diameter) to 0.90 mm. The results are shown in Table 2.

Example 3

The operation was performed by the entirely same method as in Example 1, except for changing the gas supply amount to 476 m$^3$/h. The results are shown in Table 2.

Example 4

The operation was performed by the entirely same method as in Example 1, except for changing the gas supply amount to 246 m$^3$/h. The results are shown in Table 2.

Example 5

The operation was performed by the entirely same method as in Example 1, except for changing the gas supply amount to 123 m$^3$/h. The results are shown in Table 2.

Example 6

The operation was performed by the entirely same method as in Example 1, except for changing the gas density to 40 kg/m$^3$. The results are shown in Table 2.

Example 7

The operation was performed by the entirely same method as in Example 1, except for changing the gas density to 200 kg/m$^3$. The results are shown in Table 2.

Example 8

Figure 5A:
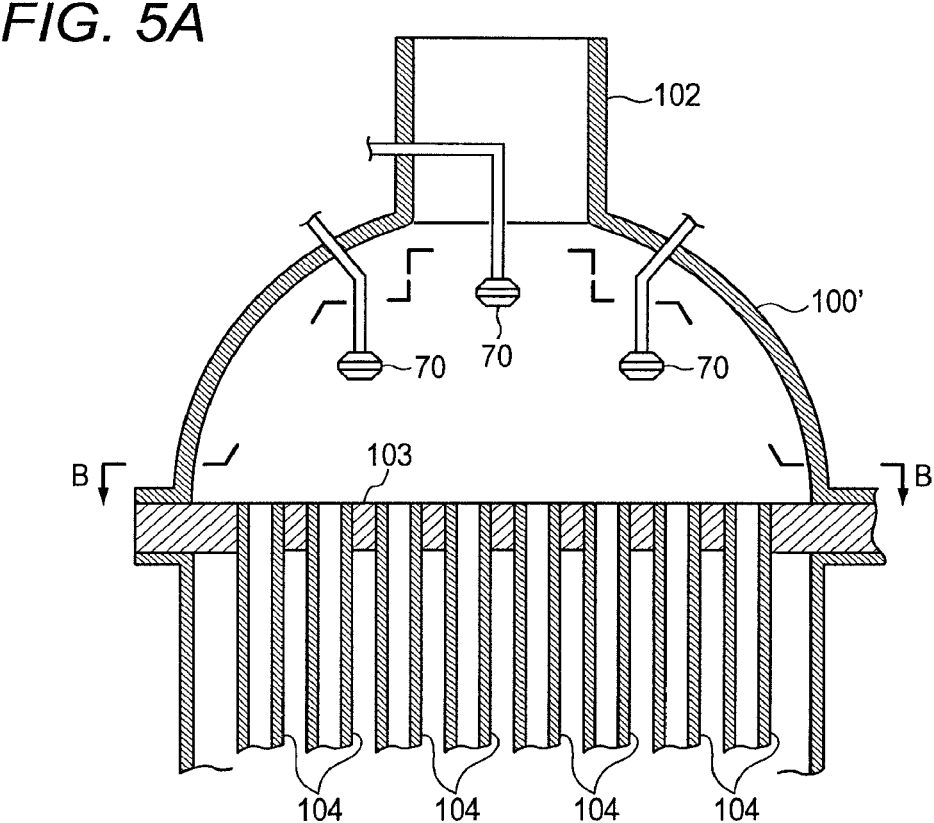
FIG. 5A is a vertical cross-sectional view showing another example of a configuration of a top cover and an upper tube plate portion of a vertical shell and tube type heat exchanger that is used in the present invention.
Figure 5B:
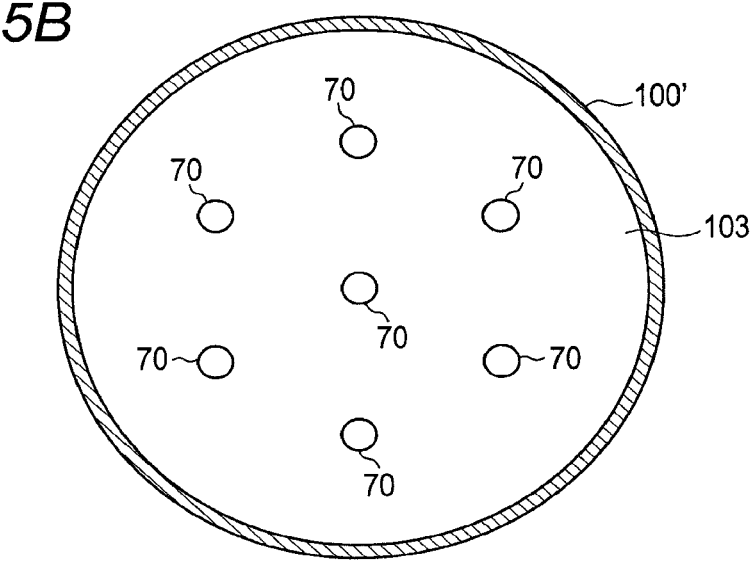
FIG. 5B is a horizontal cross-sectional view along a B-B line of FIG. 5A.
Figure 6A:
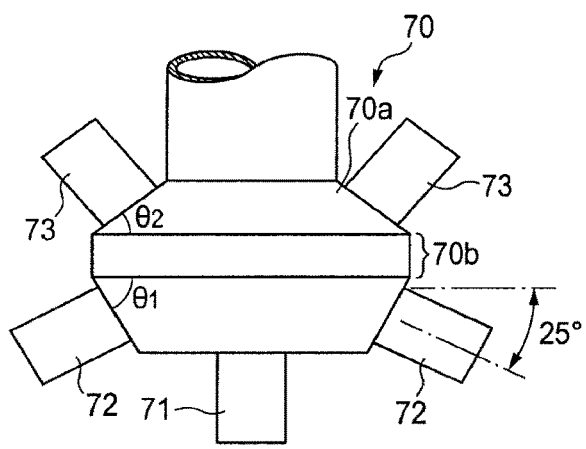
Figure 6B:
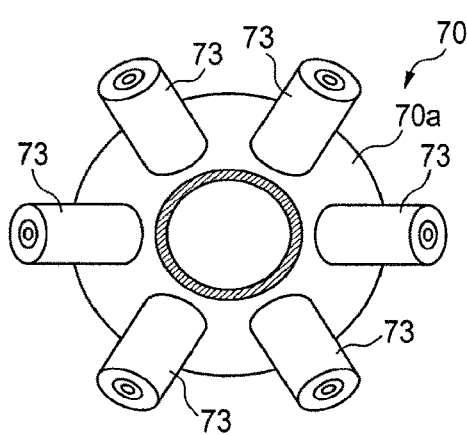
Figure 6C:
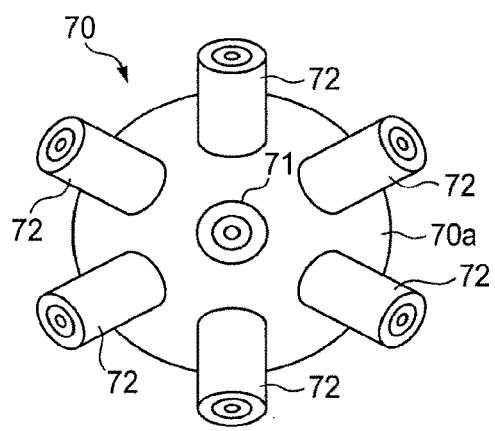

In a vertical shell and tube type heat exchanger having a top cover 100' of a semi-spherical shell shape (upper tube plate area: 2.14 m$^2$) shown in FIG. 5A, all of seven spray nozzle sets 70 each having thirteen full cone spray nozzles 71 to 73 in a nozzle body 70*a* in a disposition shown in FIG. 6A to FIG. 6C were provided in a disposition shown in FIG. 5B, thereby installing all of the ninety-one full cone spray nozzles 71 to 73. The number of spray nozzles per 1.00 m$^2$ of an area of the upper tube plate 103 was about 43.

The spray nozzle set 70 has the same nozzle disposition ($\theta_1$=65°, $\theta_2$=40°) as in the spray nozzle set 60, except for disposing six nozzles 73 on the upper surface side at six equal sites in the circumferential direction and changing the angle (elevation angle) of circumferential nozzles 72 on the lower surface side to 25°. The dimensions of a trunk part 70*b* of the nozzle body 70*a* and the dimensions of each of the nozzles are also the same as those in the spray nozzle set 60. A symbol 71 represents a central nozzle.

Figure 7:
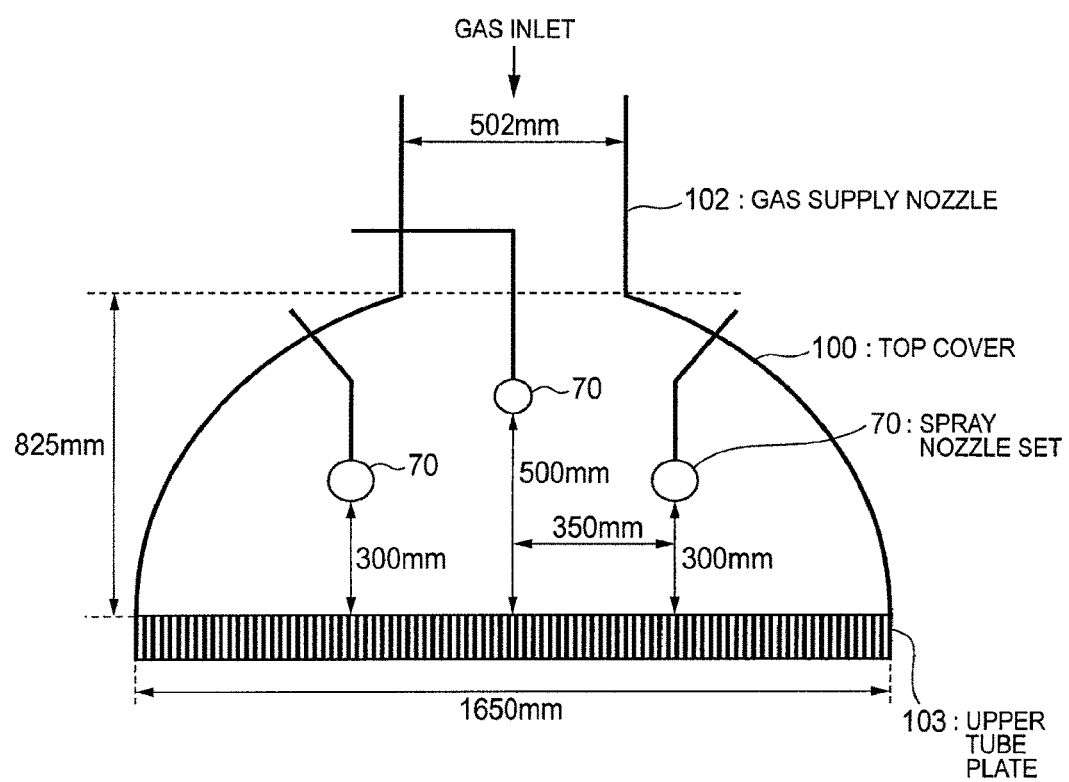
FIG. 7 is a schematic view showing dimensions of respective parts of a shell and tube type heat exchanger used in Example 8.

The instillation position of the spray nozzle set 70 and the dimensions of each of the parts of the top cover 100', the gas supply nozzle 102, and the upper tube plate 103 are shown in FIG. 7.

n-Heptane (liquid density: 600 kg/m$^3$) at a temperature of 115° C. was supplied at a rate of 204 kg/h into each of the full cone spray nozzles (designed spray angle: 60°) 71 to 73 of each of the spray nozzle sets 70 provided in the central part. A supply initial velocity of the droplet was 12 m/s, and a droplet diameter was 0.15 mm in terms of a Sauter mean diameter. n-Heptane (liquid density: 600 kg/m$^3$) at a temperature of 115° C. was supplied at a rate of 102 kg/h into each of the full cone spray nozzles (designed spray angle: 60°) 71 to 73 of each of the six spray nozzle sets 70 provided in the circumferential part. A supply initial velocity of the droplet was 15 m/s, and a droplet diameter was 0.15 mm in terms of a Sauter mean diameter. In addition, a gas having a density of 96 kg/m³ and composed mainly of ethylene, n-heptane, and 1-hexene was supplied at a flow rate of 1,447 m³/h from the gas supply nozzle (inside diameter: 502 mm, length: 500 mm) 102 of the top cover 100' of the heat exchanger.

At that time, the results of a cleaning state by n-heptane droplets on the upper surface of the upper tube plate 103 are shown in Table 2.

Example 9

Figure 8:
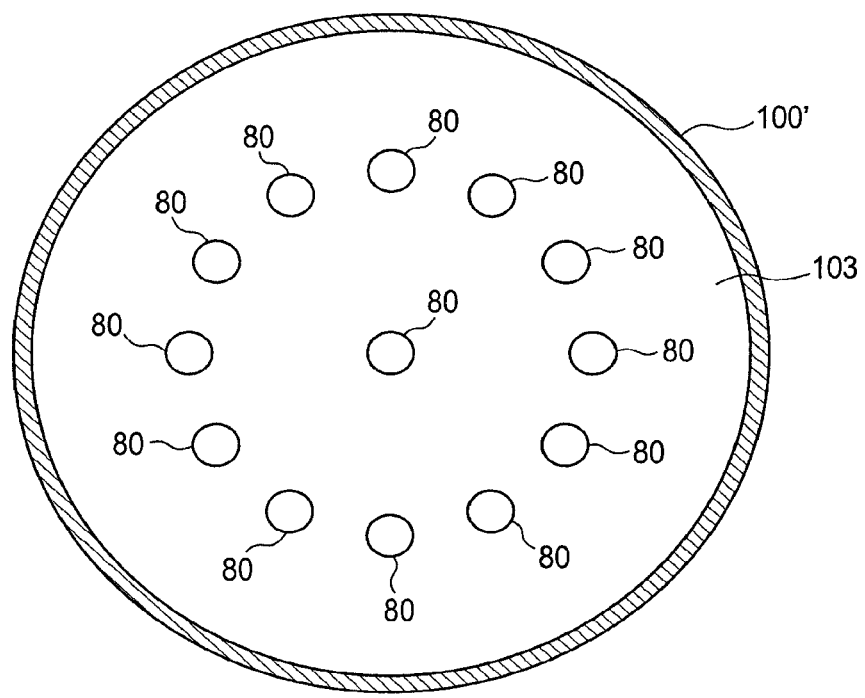
FIG. 8 is a schematic view showing disposition of a full cone spray nozzle in Example 9.

In a vertical shell and tube type heat exchanger (upper tube plate area: 2.14 m²) shown in FIG. 5A, by using one single-hole full cone spray nozzle (one nozzle) 80 in a disposition shown in FIG. 8, one full cone spray nozzle 80 and twelve full cone spray nozzles 80 were installed in the central part and the circumferential part, respectively, and all of the thirteen full cone spray nozzles 80 were installed downward (perpendicular to the tube plate surface). The number of spray nozzles per 1.00 m² of an area of the upper tube plate 103 is about 6.1. As for the dimensions of this full cone spray nozzle 80 (one nozzle), the central part has a diameter of 33 mm and a length of 53 mm, and the circumferential part has a diameter of 21 mm and a length of 35 mm.

n-Heptane (liquid density: 600 kg/m³) at a temperature of 115° C. was supplied at a rate of 2,652 kg/h into the one full cone spray nozzle (designed spray angle: 120°) 80 provided in the central part. A supply initial velocity of the droplet was 12 m/s, and a droplet diameter was 0.15 mm in terms of a Sauter mean diameter. n-Heptane (liquid density: 600 kg/m³) at a temperature of 115° C. was supplied at a rate of 663 kg/h into each of the twelve full cone spray nozzles (designed spray angle: 120°) 80 provided in the circumferential part. A supply initial velocity of the droplet was 15 m/s, and a droplet diameter was 0.15 mm in terms of a Sauter mean diameter.

The gas supply from the gas supply nozzle 102 of the top cover 100' was performed under the same conditions as in Example 8.

At that time, the results of a cleaning state by n-heptane droplets on the upper surface of the upper tube plate 103 are shown in Table 2.

Comparative Example 1

In a vertical shell and tube type heat exchanger (upper tube plate area: 2.14 m²) shown in FIG. 5A, by using one full cone spray nozzle the same as that used in Example 9 in a disposition shown in FIG. 5B, one full cone spray nozzle and six full cone spray nozzles were installed in the central part and the circumferential part, respectively, and all of the seven full cone spray nozzles were installed. The number of spray nozzles per 1.00 m² of an area of the upper tube plate 103 is about 3.3.

n-Heptane (liquid density: 600 kg/m³) at a temperature of 115° C. was supplied at a rate of 2,652 kg/h into the one full cone spray nozzle (designed spray angle: 60°) provided in the central part. A supply initial velocity of the droplet was 12 m/s, and a droplet diameter was 0.15 mm in terms of a Sauter mean diameter. n-Heptane (liquid density: 600 kg/m³) at a temperature of 115° C. was supplied at a rate of 1,326 kg/h into each of the six full cone spray nozzles (designed spray angle: 60°) provided in the circumferential part. A supply initial velocity of the droplet was 15 m/s, and a droplet diameter was 0.15 mm in terms of a Sauter mean diameter.

The gas supply from the gas supply nozzle 102 of the top cover 100' was performed under the same conditions as in Example 8.

At that time, the results of a cleaning state by n-heptane droplets on the upper surface of the upper tube plate 103 are shown in Table 2.

Reference Example 2

The operation was performed by the entirely same method as in Comparative Example 1, except for changing the density of the supply gas to 10 kg/m³. The results are shown in Table 2.

TABLE 2

|  |  | Example | | | | | |
|---|---|---|---|---|---|---|---|
|  |  | 1 | 2 | 3 | 4 | 5 | 6 |
| Operation conditions | Spray nozzle set | FIG. 3 | FIG. 3 | FIG. 3 | FIG. 3 | FIG. 3 | FIG. 3 |
|  | Number of spray nozzles | 60 | 60 | 60 | 60 | 60 | 60 |
|  | Designed spray angle of spray nozzle (°) | 60 | 60 | 60 | 60 | 60 | 60 |
|  | Upper tube plate, inside diameter (m) | 1.3 | 1.3 | 1.3 | 1.3 | 1.3 | 1.3 |
|  | Upper tube plate, area (m²) | 1.33 | 1.33 | 1.33 | 1.33 | 1.33 | 1.33 |
|  | (Number of spray nozzles)/(Upper tube plate, area (m²)) | 45 | 45 | 45 | 45 | 45 | 45 |
|  | Liquid droplet diameter (mm) | 0.15 | 0.90 | 0.15 | 0.15 | 0.15 | 0.15 |
|  | Gas flow rate within the gas supply nozzle (m/s) | 8.6 | 8.6 | 5.8 | 3.0 | 1.5 | 8.6 |
|  | Inside diameter of gas supply nozzle (m) | 0.17 | 0.17 | 0.17 | 0.17 | 0.17 | 0.17 |
|  | (Inside diameter of gas supply nozzle)/(Inside diameter of upper tube plate) | 0.13 | 0.13 | 0.13 | 0.13 | 0.13 | 0.13 |
|  | Gas density (kg/m³) | 92 | 92 | 92 | 92 | 92 | 40 |
|  | Attachment uniformity of droplets | ◯ | ◯ | ◯ | ◯ | ◯ | ◯ |

TABLE 2-continued

|  |  | Example | | | Comparative Example | Reference Example |
|---|---|---|---|---|---|---|
|  |  | 7 | 8 | 9 | 1 | 2 |
| Operation conditions | Spray nozzle set | FIG. 3 | FIG. 6 | Single hole | Single hole | Single hole |
|  | Number of spray nozzles | 60 | 91 | 13 | 7 | 7 |
|  | Designed spray angle of spray nozzle (°) | 60 | 60 | 120 | 60 | 60 |
|  | Upper tube plate, inside diameter (m) | 1.3 | 1.65 | 1.65 | 1.65 | 1.65 |
|  | Upper tube plate, area (m$^2$) | 1.33 | 2.14 | 2.14 | 2.14 | 2.14 |
|  | (Number of spray nozzles)/(Upper tube plate, area (m$^2$)) | 45 | 43 | 6.1 | 3.3 | 3.3 |
|  | Liquid droplet diameter (mm) | 0.15 | 0.15 | 0.15 | 0.15 | 0.15 |
|  | Gas flow rate within the gas supply nozzle (m/s) | 8.6 | 2.0 | 2.0 | 2.0 | 2.0 |
|  | Inside diameter of gas supply nozzle (m) | 0.17 | 0.50 | 0.50 | 0.50 | 0.50 |
|  | (Inside diameter of gas supply nozzle)/(Inside diameter of upper tube plate) | 0.13 | 0.30 | 0.30 | 0.30 | 0.30 |
|  | Gas density (kg/m$^3$) | 200 | 96 | 96 | 96 | 10 |
|  | Attachment uniformity of droplets | ○ | ○ | ○ | X | ○ |

From Examples 1 to 9, it is noted that when the gas flow rate within the gas supply nozzle of the vertical shell and tube type heat exchanger is 1 m/s or more, and the spray nozzles (jet nozzles) are installed in the number of five (five places) or more per 1.00 m$^2$ of an area of the upper tube plate, the droplet uniformity is good.

On the other hand, from Comparative Example 1, it is noted that even if the inlet gas flow rate is 1 m/s or more, in the case where the spray nozzles (jet nozzles) are installed in the number of less than five (five places) per 1.00 m$^2$ of an area of the upper tube plate, the droplet uniformity is poor.

In Reference Example 2, though the spray nozzles are installed in the number of less than five (five places) per 1.00 m$^2$ of an area of the upper tube plate, since the gas density is less than 20 kg/m$^3$, the droplet uniformity is good.

However, the gas density correlates with an ethylene partial pressure, and when the gas density is less than 20 kg/m$^3$, the catalytic activity and the reaction selectivity of the desired product are lowered, and hence, such is not preferred.

While the invention has been described in detail and with reference to specific embodiments thereof, it will be apparent to one skilled in the art that various changes and modifications can be made therein without departing from the spirit and scope thereof. It is to be noted that the present application is based on a Japanese patent application filed on Sep. 28, 2015 (Japanese Patent Application No. 2015-189298), and the contents are incorporated herein by reference.

EXPLANATIONS OF REFERENCE SIGNS

1: Production apparatus of 1-hexene
2: Reflux condensation system
10: Reactor
10*a*: Stirring machine
11*a*: Deactivator supply pipe
12: First supply pipe
12*a*: Ethylene supply pipe
13: Second supply pipe
13*a*, 13*b*: Catalyst supply tube
13*c*: Pump
15: Third supply pipe
16: Heat exchanger (condenser)
16*a*: Heat exchanger (cooling condenser)
17: Compressor
17*a*: Blower
20: Degassing tank
20*a*: Gas-liquid separator
30: Ethylene separation column
40: High boiling separation column
50: Hexene separation column
60, 70: Spray nozzle set
60*a*, 70*a*: Nozzle body
61, 62, 63, 71, 72, 73: Full cone spray nozzle
90: Shell and tube type heat exchanger
100, 100': Top cover
102: Gas supply nozzle
103: Upper tube plate
104: Tube
105: Gas reception chamber

The invention claimed is:

1. A method for oligomerizing at least one α-olefin and concurrently spraying atomized droplets in a shell and tube heat exchanger that is operatively coupled with the oligomerizing, the method comprising:
   oligomerizing the α-olefin in an oligomerization reactor in the presence of a catalyst to produce at least one α-olefin oligomer, wherein the reactor comprises a gas phase and a liquid phase;
   withdrawing a portion of the gas from the gas phase of the oligomerization reactor;
   introducing the withdrawn gas through a gas supply port into the shell and tube heat exchanger, wherein the introduced gas has a density of 20 kg/m$^3$ or more, and the gas flow rate of the introduced gas from the gas supply port is 1 m/s or more;
   cooling the introduced gas in the shell and tube heat exchanger to obtain a condensed liquid;
   recycling a portion of the condensed liquid into the reactor; and
   supplying into the shell and tube heat exchanger atomized droplets of a portion of the condensed liquid, of a liquefied α-olefin, and/or of a circulation solvent from the bottom of a downstream separation column,
wherein:
the shell and tube heat exchanger comprises jet nozzles for supplying the atomized droplets between the gas supply port and a tube plate disposed in a horizontally opposite direction to the gas supply port in the shell and tube heat exchanger;
five or more of the jet nozzles are provided per $1.00\ m^2$ of an area of the tube plate; and
the jet nozzles include at least one nozzle that is inclined toward the gas supply port from the horizontal direction.

2. The method according to claim 1, wherein the atomized droplets comprise the condensed liquid.

3. The method according to claim 1, wherein a Sauter mean diameter of the atomized droplets is 3 mm or less.

4. The method according to claim 1, wherein the jet nozzles comprise a spray nozzle.

5. The method according to claim 1, wherein the α-olefin is ethylene.

6. The method according to claim 1, wherein the jet nozzles comprise a full cone spray nozzle.

7. The method according to claim 6, wherein a spray angle of the full cone spray nozzle is 15° to 170°.

8. The method according to claim 1, wherein the jet nozzles also include at least one radially obliquely upward nozzle, in which radially obliquely upward is relative to an axis of the tube plate.

9. The method according to claim 1, wherein the jet nozzles include at least one vertically downward central nozzle and at least one radially obliquely downward nozzle, in which vertically downward and radially obliquely downward are relative to an axis of the tube plate.

10. The apparatus according to claim 1, wherein the jet nozzles protrude from the top cover of the heat exchanger.

11. A method for oligomerizing at least one α-olefin and concurrently spraying atomized droplets in a heat exchanger that is operatively coupled with the oligomerizing, the method comprising:
oligomerizing the α-olefin in an oligomerization reactor in the presence of a catalyst to produce at least one α-olefin oligomer, wherein the reactor comprises a gas phase and a liquid phase;
withdrawing a portion of the gas from the gas phase of the oligomerization reactor;
introducing the withdrawn gas through a gas supply nozzle into the heat exchanger, wherein the introduced gas has a density of $20\ kg/m^3$ or more, and the gas flow rate of the introduced gas from the gas supply port is 1 m/s or more;
cooling the introduced gas in the heat exchanger to obtain a condensed liquid;
recycling a portion of the condensed liquid into the reactor; and
supplying into the heat exchanger atomized droplets of a portion of the condensed liquid, of a liquefied α-olefin, and/or of a circulation solvent from the bottom of a downstream separation column,
wherein:
i) the heat exchanger comprises:
a cylindrical shell;
an upper tube plate and a lower tube plate disposed on an upper end side and a lower end side of the shell, respectively;
a plurality of tubes installed between the upper tube plate and the lower tube plate;
a top cover disposed on the upper side of the upper tube plate wherein the gas supply nozzle is provided in the top cover;
a bottom cover disposed on the lower side of the lower tube plate;
and
a takeout port provided in the bottom of the bottom cover for removing the condensed liquid;
ii) the heat exchanger comprises jet nozzles for supplying the atomized droplets between the gas supply port and the upper tube plate;
iii) five or more jet nozzles are provided per $1.00\ m^2$ of a surface area of the upper tube plate; and
iv) the jet nozzles include at least one nozzle that is inclined toward the gas supply nozzle from the horizontal direction.

12. The method according to claim 11, wherein the jet nozzles also include at least one radially obliquely upward nozzle, in which radially obliquely upward is relative to an axis of the upper tube plate.

13. The method according to claim 11, wherein the jet nozzles include at least one vertically downward central nozzle and at least one radially obliquely downward nozzle, in which vertically downward and radially obliquely downward are relative to an axis of the upper tube plate.

14. The apparatus according to claim 11, wherein the jet nozzles protrude from the top cover of the heat exchanger.

15. An apparatus, comprising:
an oligomerization reactor in which a catalyst and at least one α-olefin are supplied to oligomerize the α-olefin wherein the oligomerization reactor comprises a gas phase and a liquid phase;
a piping connected to the gas phase of the reactor on one end;
a shell and tube heat exchanger comprising a gas supply nozzle that is connected to the other end of the piping wherein a gas withdrawn from the gas phase from the reactor is cooled in the shell and tube heat exchanger to obtain a condensed liquid; and
a takeout port piping connecting the heat exchanger and the reactor for recycling of the condensed liquid into the oligomerization reactor,
wherein:
i) the heat exchanger further comprises:
a cylindrical shell;
an upper tube plate and a lower tube plate disposed on an upper end side and a lower end side of the shell, respectively;
a plurality of tubes installed between the upper tube plate and the lower tube plate;
a top cover disposed on the upper side of the upper tube plate wherein the gas supply nozzle is provided in the top cover; and
a bottom cover disposed on the lower side of the lower tube plate wherein the takeout port is provided in the bottom of the bottom cover;
ii) the gas supply nozzle is adapted to function such that the gas is introduced into the heat exchanger at a density of $20\ kg/m^3$ or more and at a gas flow rate of 1 m/s or more;
iii) the top cover further comprises jet nozzles for supplying atomized droplets onto the surface of the upper tube plate;
iv) five or more of the jet nozzles are provided per $1.00\ m^2$ of an area of the upper tube plate; and v) the jet nozzles include at least one nozzle that is inclined toward the gas supply nozzle from the horizontal direction.

16. The apparatus according to claim 15, wherein the jet nozzles comprise a spray nozzle.

17. The apparatus according to claim 15, wherein:
the jet nozzles protrude from the top cover; and
a direction of the atomized droplets supplied from the jet nozzles is inclined relative to a direction of the gas introduced from the gas supply nozzle from the horizontal direction.

18. The apparatus according to claim 15, wherein the jet nozzles comprise a full cone spray nozzle.

19. The apparatus according to claim 18, wherein a spray angle of the full cone spray nozzle is 15° to 170°.

20. The apparatus according to claim 15, wherein the jet nozzles also include at least one radially obliquely upward nozzle, in which radially obliquely upward is relative to an axis of the upper tube plate.

21. The apparatus according to claim 15, wherein the jet nozzles include at least one vertically downward central nozzle and at least one radially obliquely downward nozzle, in which vertically downward and radially obliquely downward are relative to an axis of the upper tube plate.

22. The apparatus according to claim 15, wherein the jet nozzles protrude from the top cover of the heat exchanger.

* * * * *